(12) United States Patent
Wang et al.

(10) Patent No.: US 12,729,361 B2
(45) Date of Patent: Sep. 8, 2026

(54) CULTURE STRUCTURE, CULTURE METHOD AND CULTURE CHIP

(71) Applicant: BOE Technology Group Co., Ltd., Beijing (CN)

(72) Inventors: Shicai Wang, Beijing (CN); Ding Ding, Beijing (CN)

(73) Assignee: BOE Technology Group Co., Ltd., Beijing (CN)

( * ) Notice: Subject to any disclaimer, the term of this patent is extended or adjusted under 35 U.S.C. 154(b) by 739 days.

(21) Appl. No.: 18/038,992

(22) PCT Filed: Jun. 29, 2022

(86) PCT No.: PCT/CN2022/102417
§ 371 (c)(1),
(2) Date: May 26, 2023

(87) PCT Pub. No.: WO2024/000286
PCT Pub. Date: Jan. 4, 2024

(65) Prior Publication Data

US 2024/0352394 A1 Oct. 24, 2024

(51) Int. Cl.

*C12M 3/06* (2006.01)
*C12M 1/00* (2006.01)
*C12M 1/32* (2006.01)

(52) U.S. Cl.

CPC ............ *C12M 27/16* (2013.01); *C12M 23/12* (2013.01); *C12M 23/16* (2013.01); *C12M 23/38* (2013.01)

(58) Field of Classification Search

None
See application file for complete search history.

(56) References Cited

U.S. PATENT DOCUMENTS 5,413,770 A 5/1995 Sakaguchi et al.
2004/0033588 A1 2/2004 Su et al.
2005/0277184 A1 12/2005 Bargh
2017/0014787 A1 1/2017 Douglas et al.
(Continued)

FOREIGN PATENT DOCUMENTS

CN 106660047 A 5/2017
CN 112553076 A 3/2021
(Continued)

OTHER PUBLICATIONS

Hongwei Cai et al., "Trapping cell spheroids and organoids using digital acoustofluidics", 2020 Biofabrication 12 035025.
(Continued)

*Primary Examiner* — P. Kathryn Wright

(57) ABSTRACT

A culture structure, a culture method and a culture chip are provided. The culture structure includes a culture plate and a vibration structure provided on the culture plate; the culture plate includes a plurality of accommodating structures configured to accommodate culture solution; the vibration structure includes a vibration signal generating structure and a plurality of vibration members; the vibration signal generating structure is configured to generate a vibration signal; the plurality of vibration members are connected to the vibration signal generating structure and configured to drive the culture solution in the plurality of accommodating structures to move according to the vibration signal.

16 Claims, 13 Drawing Sheets

(56) References Cited

U.S. PATENT DOCUMENTS

| | | | | |
|---|---|---|---|---|
| 2017/0136456 | A1 | 5/2017 | Chen et al. | |
| 2018/0008944 | A1 | 1/2018 | Ozeki | |
| 2018/0292393 | A1 | 10/2018 | Neilson et al. | |
| 2020/0216789 | A1 * | 7/2020 | Pizzi ...................... | C12M 23/12 |
| 2021/0379592 | A1 | 12/2021 | Hui et al. | |

FOREIGN PATENT DOCUMENTS

| | | | |
|---|---|---|---|
| CN | 113773959 | A | 12/2021 |
| CN | 215593084 | U | 1/2022 |
| WO | 2017127686 | A1 | 7/2017 |

OTHER PUBLICATIONS

Kejie Chen et al., "Rapid formation of size-controllable multicellular spheroids via 3D acoustic tweezers", Lab Chip., pp. 1-16, Jul. 2016.

Si Li Liu et al., "Effect of sonic stimulation on Bacillus endospore germination", FEMS Microbiology Letters, 2016, vol. 363, No. 1.

Yuta Kurashina et al., "Cell agglomeration in the wells of a 24-well plate using acoustic streaming", Lab Chip, 2017, 17, 876-886.

* cited by examiner

CULTURE STRUCTURE, CULTURE METHOD AND CULTURE CHIP

CROSS-REFERENCE TO RELATED APPLICATION

The present application is a U.S. National Phase Entry of International Application No. PCT/CN2022/102417 having an international filing date of Jun. 29, 2022, the entire content of which is hereby incorporated by reference.

TECHNICAL FIELD

Embodiments of the present disclosure relate to, but are not limited to, the field of biotechnology, in particular to a culture structure, a culture method and a culture chip.

BACKGROUND

In recent years, with the development of cell biology and tissue engineering, three-dimensional cell model is gradually replacing the traditional two-dimensional cell model. As a new three-dimensional research model in vitro, organoid is self-assembled by stem cells in vitro, and grows and develops into three-dimensional aggregates similar to human tissues or organs in structure and function, such as brain organs, vascular organs, liver organs, kidney organs and tumor organs.

SUMMARY

The following is a summary of subject matters described herein in detail. The summary is not intended to limit the protection scope of claims.

In the first aspect, the present disclosure provides a culture structure including a culture plate and a vibration structure provided on the culture plate. The culture plate includes a plurality of accommodating structures configured to accommodate culture solution. The vibration structure includes a vibration signal generating structure and a plurality of vibration members. The vibration signal generating structure is configured to generate a vibration signal. The plurality of vibration members are connected to the vibration signal generating structure and configured to drive the culture solution in the plurality of accommodating structures to move according to the vibration signal.

In an exemplary embodiment, the vibration structure further includes a cover plate; the accommodating structure includes an opening arranged to face a side of the cover plate; the cover plate is provided on a side of the culture plate located at the opening of the accommodating structure. The plurality of vibration members are provided on a side of the cover plate facing the culture plate, and any one of the vibration members is arranged corresponding to one of the accommodating structures; the vibration member includes a first end and a second end which are arranged opposite to each other, the first end of the vibration member is connected to the cover plate, and the second end of the vibration member extends away from the cover plate into the culture solution of a corresponding accommodating structure. The vibration signal generating structure is provided on the cover plate, connected to the plurality of vibration members through the cover plate, and applies the vibration signal to the vibration members through the cover plate.

In an exemplary embodiment, the vibration signal generating structure includes at least two piezoelectric transducers provided at an edge of the cover plate, and propagation directions of the vibration signals generated by the at least two piezoelectric transducers intersect with each other in a plane where the cover plate is located.

In an exemplary embodiment, the vibration signal generating structure includes two piezoelectric transducers, and an angle between the propagation directions of the vibration signals generated by the two piezoelectric transducers is 80° to 100° in the plane where the cover plate is located.

In the exemplary embodiment, the cover plate is a rectangular structure, the two piezoelectric transducers are provided on two sides of the cover plate that are perpendicular to each other, and the propagation directions of the vibration signals generated by the two piezoelectric transducers are orthogonal in the plane where the cover plate is located.

In an exemplary embodiment, the vibration signal generating structure includes a plurality of piezoelectric transducers respectively corresponding to the plurality of vibration members, and a vibration signal generated by each piezoelectric transducer is applied to a corresponding vibration member.

In an exemplary embodiment, a depth of the culture solution is 1 mm to 4 mm, a depth of the vibration member extending to the culture solution of the corresponding accommodating structure is 0.5 mm to 3 mm, and a distance between the vibration member and a bottom of the accommodating structure is 0.5 mm to 1.5 mm.

In an exemplary embodiment, orthographic projections of the plurality of vibration members on the culture plate are located within a range of orthographic projections of the plurality of accommodating structures on the culture plate.

In an exemplary embodiment, an area of the orthographic projection of the vibration member on the culture plate is 30% to 70% of an area of the orthographic projection of the accommodating structure corresponding to the vibration member on the culture plate.

In an exemplary embodiment, the vibration member is a vertebral structure, and an area of an orthographic projection of a first end of the vibration member on the cover plate is larger than an area of an orthographic projection of a second end of the vibration member on the cover plate.

In an exemplary embodiment, end faces of the first end and the second end of the vibration member are both circular, a diameter of an end face of the first end of the vibration member is 0.4 mm to 0.8 mm, a diameter of an end face of the second end of the vibration member is 0.1 mm to 0.3 mm, and the accommodating structure is a hollow cylindrical structure with an inner diameter of 14 mm to 18 mm.

In an exemplary embodiment, the vibration member is a column structure, and end faces of the first end and the second end of the column structure are both circular.

In an exemplary embodiment, diameters of the end faces of the first end and the second end of the column structure are 0.1 mm to 6 mm, the accommodating structure is a hollow cylindrical structure or a hollow cuboid structure, an inner diameter of the hollow cylindrical structure is 0.5 mm to 26 mm, an opening position of the accommodating structure of the hollow cuboid structure is square, a side length of the square opening position is 0.5 mm to 26 mm, and a plane where the opening position is located is parallel to a plane where the cover plate is located. An orthographic projection of the column structure on the cover plate falls within a range of an orthographic projection of the accommodating structure on the cover plate.

In an exemplary embodiment, the diameters of the end faces of the first end and the second end of the column structure are 0.1 mm to 0.4 mm. The inner diameter of the hollow cylindrical structure is 0.5 mm to 1.5 mm, and the side length of the square opening position is 0.5 mm to 1.5 mm.

In an exemplary embodiment, the diameters of the end faces of the first end and the second end of the column structure are 1 mm to 6 mm. The inner diameter of the hollow cylinder is 10 mm to 26 mm, and the side length of the square opening position is 10 mm to 26 mm.

In an exemplary embodiment, an input voltage signal of the piezoelectric transducer is 0.3 V to 0.8 V, a frequency of the input voltage signal is 25 kHz to 35 kHz, and a phase difference of the vibration signals generated by the two piezoelectric transducers is −10° to 10°.

In an exemplary embodiment, the vibration member is a cuboid structure, the accommodating structure is a hollow cuboid structure, and an orthographic projection of the accommodating structure on the cover plate covers an orthographic projection of the vibration member on the cover plate.

In an exemplary embodiment, end faces of the first end and the second end of the cuboid structure are both square, and a side length of the square is 4 mm to 12 mm; and an opening position of the accommodating structure is square, a side length of the square opening position is 14 mm to 22 mm, and a plane where the opening position is located is parallel to a plane where the cover plate is located.

In an exemplary embodiment, the vibration member is a column structure, end faces of the first end and the second end of the column structure are circular, any one of the accommodating structures is corresponding to two column structures, and orthographic projections of the two column structures on the cover plate are within a range of orthographic projections of corresponding accommodating structure on the cover plate.

In an exemplary embodiment, diameters of the end faces of the first end and the second end of the column structure are 0.1 mm to 0.4 mm; a spacing between two vibration members corresponding to the same accommodating structure is 0.1 mm to 0.3 mm. The accommodating structure is a hollow cylindrical structure, and an inner diameter of the hollow cylindrical structure is 1.1 mm to 3.2 mm; or the accommodating structure is a hollow cuboid structure, an opening position of the accommodating structure is a square, a side length of the square opening position is 1.1 mm to 3.2 mm, and a plane where the opening position is located is parallel to a plane where the cover plate is located.

In an exemplary embodiment, the diameters of the end faces of the first ends and the second ends of the plurality of the vibration members gradually decrease from being close to the piezoelectric transducer to being away from the piezoelectric transducer.

In an exemplary embodiment, side lengths of the end faces of the first ends and the second ends of the plurality of the vibration members gradually decrease from being close to the piezoelectric transducer to being away from the piezoelectric transducer.

In an exemplary embodiment, the vibration signal generating structure includes a plurality of piezoelectric transducers, the vibration members are located at positions of a bottom of the culture plate is corresponding to the plurality of accommodating structures respectively, the plurality of piezoelectric transducers are respectively corresponding to the plurality of vibration members, and a vibration signal generated by each piezoelectric transducer is applied to the corresponding vibration member.

In an exemplary embodiment, the piezoelectric transducer is an annular piezoelectric transducer; and an orthographic projection of the piezoelectric transducer on the cover plate is at least partially overlapped with an orthographic projection of the corresponding vibration member on the cover plate.

In an exemplary embodiment, an input voltage signal of the piezoelectric transducer is 0.3 V to 0.8 V, a frequency of the input voltage signal is 20 kHz to 40 kHz, and a phase difference of the vibration signals generated by the two piezoelectric transducers is 80° to 100°.

In an exemplary embodiment, a thickness of the culture plate is 15 mm to 21 mm, and a height of the vibration member is 14 mm to 20 mm.

In the second aspect, an embodiment of the present disclosure further provides a culture method, which adopts the culture structure described in any one of the above embodiments to culture an organoid, wherein the culture structure includes a culture plate and a vibration structure, the culture plate includes a plurality of accommodating structures, the accommodating structures are configured to accommodate culture solution, and the vibration structure includes a vibration signal generating structure and a plurality of vibration members.

The method including following acts: generating a vibration signal; and driving, by the vibration structure, the culture solution in the accommodating structure to move according to the vibration signal.

In an exemplary embodiment, the vibration structure further includes a cover plate. The accommodating structure includes an opening arranged to face a side of the cover plate, and the cover plate is provided on a side of the culture plate located at the opening of the accommodating structure. The plurality of vibration members are provided on a side of the cover plate facing the culture plate, and any one of the vibration members is arranged corresponding to one of the accommodating structures; the vibration member includes a first end and a second end which are arranged opposite to each other, the first end of the vibration member is connected to the cover plate, the second end of the vibration member extends away from the cover plate into the culture solution of the corresponding accommodating structure; and the vibration signal generating structure is provided on the cover plate.

The act of generating the vibration signal includes applying a voltage signal to the vibration signal generating structure, and generating a vibration signal, by the vibration signal generating structure, according to the voltage signal.

The act of driving, by the vibration structure, the culture solution in the accommodating structure to move according to the vibration signal, includes applying the vibration signal to the vibration member through the cover plate, and driving, by the vibration member, the culture solution in the corresponding accommodating structure to move.

In the third aspect, an embodiment of the present disclosure further provides a culture chip including the culture structure described in any one of the above embodiments.

Of course, an implementation of any product or method in the embodiments of the present disclosure does not need to achieve all the advantages mentioned above at the same time. Other features and advantages of the present disclosure will be described in subsequent embodiments in the description, and, in part, become apparent from the embodiments in the description, or can be understood by implementing the embodiments of the present disclosure. Purposes and other advantages of the technical solutions of the present disclosure may be achieved and acquired by structures specified in the detailed description, claims and drawings.

Other aspects may be understood upon reading and understanding the drawings and the detailed description.

BRIEF DESCRIPTION OF DRAWINGS

The drawings are intended to provide a further understanding of technical solutions of the present disclosure and form a part of the specification, and are used to explain the technical solutions of the present disclosure together with embodiments of the present disclosure, but not intended to form limitations on the technical solutions of the present disclosure. Shapes and sizes of components in the drawings do not reflect actual scales, but are only intended to schematically illustrate contents of the present disclosure.

DETAILED DESCRIPTION

Figure 1:
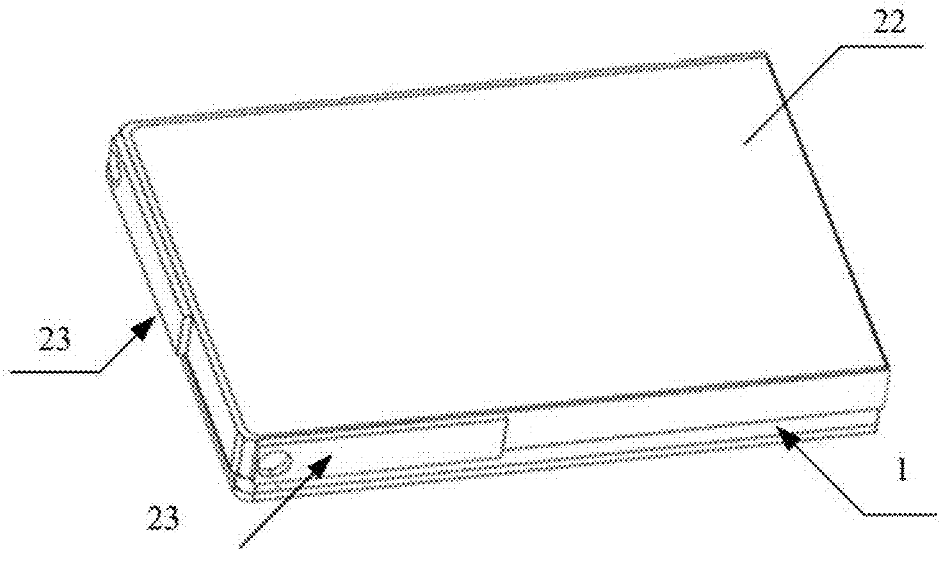
FIG. 1 is a schematic diagram of a three-dimensional structure of a culture structure according to an embodiment of the present disclosure.

Following embodiments serve to illustrate the present disclosure, but are not intended to limit the scope of the present disclosure. It is to be noted that the embodiments in the present disclosure and features in the embodiments may be randomly combined with each other if there is no conflict.

In the culture structure provided by an embodiment of the present disclosure, "thickness", "height" and "depth" refer to the dimensions along the direction perpendicular to the plane of the culture plate (or the plane of the cover plate).

An organoid refers to an organ-like tissue structure with relatively stable phenotype and genetic characteristics cultured in vitro by 3D culture technology, which is of great significance in the study of growth and development, physiology and pathology, drug effects and so on. However, in the process of culturing an organoid, the following phenomena always occur, such as uneven growth and development of the organoid, incomplete development of the organoid and even death of the organoid cell due to the lack of oxygen or nutrients in the center during the organoid growth.

Accordingly, an embodiment of the present disclosure provides a culture structure. As shown in FIGS. 1, 2, 5, 7, 9 and 11, the culture structure may include a culture plate 1 and a vibration structure 2 provided on the culture plate 1.

The culture plate 1 may include a plurality of accommodating structures 11 configured to accommodate culture solution 3.

The vibration structure 2 may include a vibration signal generating structure 23 and a plurality of vibration members 21.

The vibration signal generating structure 23 is configured to generate a vibration signal.

The plurality of vibration members 21 are connected to the vibration signal generating structure 23 and configured to drive the culture solution 3 in the plurality of accommodating structures 11 to move according to the vibration signal.

The culture structure provided by an embodiment of the present disclosure includes a culture plate and a vibration structure, wherein the culture plate includes a plurality of accommodating structures for accommodating culture solution, the vibration structure includes a vibration signal generating structure and a plurality of vibration members, and the plurality of vibration members drive the culture solution in the plurality of accommodating structures to move according to the vibration signal generated by the vibration signal generating structure.

In an embodiment of the present disclosure, the culture structure may be used to culture an organoid or culture cells.

According to the culture structure provided by an embodiment of the present disclosure, since the plurality of vibration members drive the culture solution in the plurality of accommodating structures to move according to the vibration signal generated by the vibration signal generating structure, sufficient oxygen may be provided to the organoid in the process of organoid growth, and the oxygen and nutrients in the culture solution are balanced, so that the organoid cultured in the culture solution develops completely, thereby solving the technical problem that the organoid cell dies due to the lack of oxygen or nutrients in the center during the organoid growth.

In an exemplary embodiment, since the plurality of vibration members 21 drive the culture solution 3 in the plurality of accommodating structures 11 to move according to the vibration signal, the vibration members 21 may drive particles in the culture solution in the accommodating structures 11 to rotate around the vibration members 21 according to the vibration signal, or the vibration members 21 drive the particles in the culture solution in the accommodating structures 11 to vibrate according to the vibration signal.

The vibration member 31 in the culture structure provided by an embodiment of the present disclosure may be adjusted into a corresponding size according to actual requirements so as to match various application scenarios. The culture structure of an embodiment of the present disclosure has a simple overall structure and low preparation cost, and can be prepared in batches using a processing technology, which is conducive to large-scale popularization and application.

In an exemplary embodiment, as shown in FIGS. 1, 2, 5, 7, 9 and 11, the vibration structure 2 may further include a cover plate 22; the accommodating structure 11 includes an opening 110 arranged to face a side of the cover plate 22; the cover plate 22 is provided on a side of the culture plate 1 located at the opening 110 of the accommodating structure 11; the plurality of vibration members 21 are provided on a side of the cover plate 22 facing the culture plate 1, and any one of the vibration members 21 is arranged corresponding to one of the accommodating structures 11; the vibration member 21 includes a first end 211 and a second end 212 arranged oppositely, the first end 211 of the vibration member 21 being connected to the cover plate 22, the second end 212 of the vibration member 21 extending away from the cover plate 22 into the culture solution 3 of the corresponding accommodating structure 11 and being not in contact with the accommodating structure and the culture plate; the vibration signal generating structure 23 is provided on the cover plate 22, and connected to the plurality of vibration members 21 through the cover plate 22 to generate a vibration signal, and apply the vibration signal to the plurality of vibration members 21 through the cover plate 22 to cause the plurality of vibration members 21 to generate vibration, thereby driving the culture solution 3 in the plurality of accommodating structures 11 to move, increasing the oxygen in the culture solution 3, and balancing the oxygen and nutrients in the culture solution 3.

In an embodiment of the present disclosure, the vibration signal generated by the vibration signal generating structure 23 may be a bulk acoustic wave.

In an exemplary embodiment, as shown in FIGS. 1, 2, 5, 7, 9 and 11, the vibration signal generating structure 23 may include at least two piezoelectric transducers 231 arranged at an edge of the cover plate 22, and propagation directions of the vibration signals generated by the at least two piezoelectric transducers 231 intersect with each other in a plane where the cover plate 22 is located.

In an exemplary embodiment, as shown in FIGS. 1, 2, 5, 7, 9 and 11, the vibration signal generating structure 23 may include two piezoelectric transducers 231, and an angle between propagation directions of the vibration signals generated by the two piezoelectric transducers 231 is 80° to 100° in a plane where the cover plate 22 is located. For example, the angle between the propagation directions of the vibration signals generated by the two piezoelectric transducers 231 is 90°. That is, the propagation directions of the vibration signals generated by the two piezoelectric transducers 231 are orthogonal in the plane where the cover plate 22 is located.

In an embodiment of the present disclosure, a bulk acoustic wave vibration signal generated by excitation of the two piezoelectric transducers 231 couples the cover plate 22 to vibrate. The vibration of the cover plate 22 causes forced vibration of the vibration member 21 coupled to a lower surface thereof, and the culture solution 3 moves in a velocity gradient perpendicular to the direction of the vibration member 21 under the action of the acoustic wave.

In an exemplary embodiment, as shown in FIGS. 2, 5, 7, 9 and 11, the cover plate 22 is a rectangular structure, two piezoelectric transducers 231 are provided on two sides of the cover plate 22 that are perpendicular to each other, and the propagation directions of the vibration signals generated by the two piezoelectric transducers 231 are orthogonal in the plane where the cover plate 22 is located.

In an exemplary embodiment, the input voltage signal of the piezoelectric transducer is 0.3 V to 0.8 V, the frequency of the input voltage signal is 20 kHz to 40 kHz, and the phase difference between the vibration signals generated by the two piezoelectric transducers is 80° to 100°. For example, in the culture structure shown in FIGS. 2, 5, 9 and 11, the input voltage signal of the piezoelectric transducer is 0.5 V, the frequency of the input voltage signal is 30 kHz, and the phase difference between the two orthogonal piezoelectric transducers is 90°. In an exemplary embodiment, in the culture structure shown in FIG. 7, the piezoelectric transducer 231 has an input voltage signal of 0.3 V to 0.8 V, the frequency of the input voltage signal is 25 kHz to 35 kHz, and the phase difference between the vibration signals generated by the two piezoelectric transducers is −10° to 10°. For example, in the culture structure shown in FIG. 7, two piezoelectric transducers are orthogonal, the phase difference of vibration signals generated by the two piezoelectric transducers 231 is 0°, the input voltage signal of the piezoelectric transducer 231 is 0.5 V, and the frequency of the input voltage signal is 30 KHz.

In an embodiment of the present disclosure, when two mutually orthogonal piezoelectric transducers 231 input the same signal (same phase) to excite the same vibration member 21, two or more symmetrical annular acoustic flow fields are generated around the vibration member 21; and the same vibration member 21 is excited when the phase difference between the input signal periods of two mutually orthogonal piezoelectric transducers 231 is a half period, one or more circular acoustic flow fields are generated around the vibration member 21. The acoustic flow field enables the organoid to rotate along the vibration member. On the one hand, it may realize the active periodic movement of the organoid to solve the death problem caused by lack of oxygen; on the other hand, it may balance the nutrients in the culture solution and avoid central lack of oxygen.

In an embodiment of the present disclosure, the plurality of vibration members are used as transmission media of vibration signals, the swirl flow field of the culture solution in the accommodating structure of the culture plate is constructed by regulating the phase of the input vibration signal of the piezoelectric transducer, such that the particles in the culture solution rotate uniformly, and the continuously rotating fluid ensures the uniform distribution of nutrients and oxygen, provides sufficient supply to the organoid, and improves the survival rate of the organoid, thereby solving the problems such as lack of oxygen of the organoid in the culture solution on the culture plate. In an embodiment of the present disclosure, since the selected acoustic wave frequency is below 100 kHz, the corresponding acoustic wavelength in the device is on the order of centimeters, and the bulk acoustic wave is generated within several periods without obvious additional effect, the size and shape of the selected transducers do not have a decisive influence on the result, and their orthogonal positions directly determine the flow result.

In an embodiment of the present disclosure, a plurality of accommodating structures 11 for accommodating culture solution are provided on the culture plate 1, the vibration structure 2 includes a plurality of vibration members 21, the vibration members 21 are corresponding to the plurality of accommodating structures 11, and each organoid may be cultured separately in the culture solution of one accommodating structure 11, so that a plurality of organoids are prevented from fusing with each other, the sizes and shapes of the formed organoids are relatively uniform, and therefore the culture structure may produce organoids with the same size in batches, and standardized organoid culture is realized.

In an exemplary embodiment, the vibration signal generating structure 23 may include a plurality of piezoelectric transducers respectively corresponding to a plurality of vibration members 21, and a vibration signal generated by each piezoelectric transducer is applied to the corresponding vibration member 21. For example, a plurality of identical piezoelectric transducers may be provided on the cover plate 22, or a piezoelectric transducer may be provided on each vibration member 21, the same signal may be applied to the plurality of piezoelectric transducers, and the vibration signal generated by each piezoelectric transducer is applied to the vibration member corresponding to the piezoelectric transducer. In an embodiment of the present disclosure, the piezoelectric transducer may be an annular piezoelectric transducer. A plurality of annular piezoelectric transducers are respectively corresponding to a plurality of vibration members 21, and an orthographic projection of the annular piezoelectric transducer on the cover plate is at least partially overlapped with an orthographic projection of the vibration members 21 on the cover plate.

In an embodiment of the present disclosure, the vibration signal generating structure 23 generates a vibration signal, and the vibration member 21 drives the culture solution to move according to the vibration signal. Since the vibration signals received by the plurality of vibration members 21 are relatively consistent, the movement of the culture solution in the plurality of accommodating structures 11 driven by the plurality of vibration members 21 is similar, so that a difference in movements among a plurality of simultaneously cultured array-organoids having the same movement trajectory and subjected to similar forces may be reduced, which is helpful to realize the standardized culture of organoids.

Figure 2A:
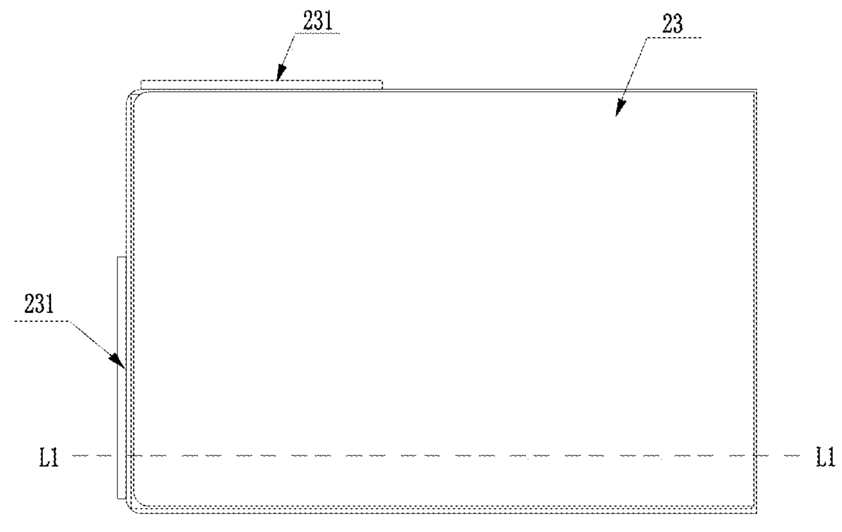
FIG. 2*a* is a schematic diagram of a planar structure of a culture structure according to an exemplary embodiment of the present disclosure.
Figure 2B:
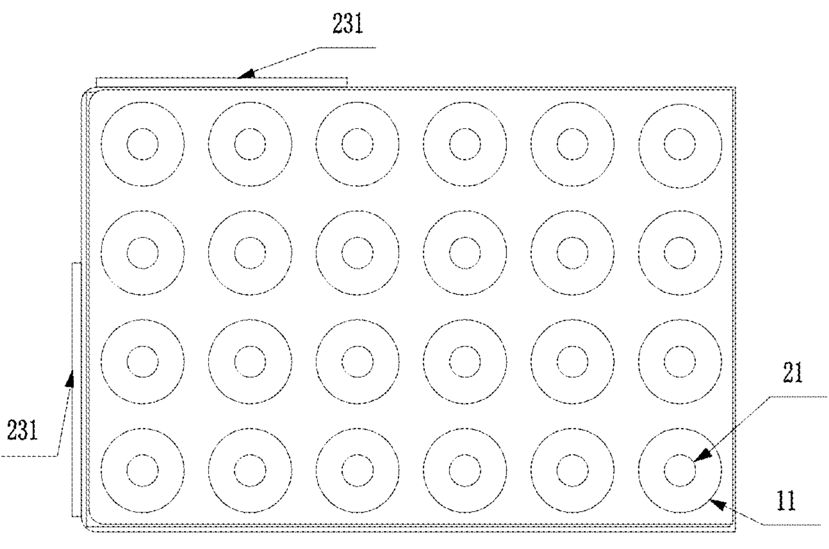
FIG. 2*b* is a schematic diagram of a planar structure of a culture structure shown in FIG. 2*a* with a cover plate removed.
Figure 2C:
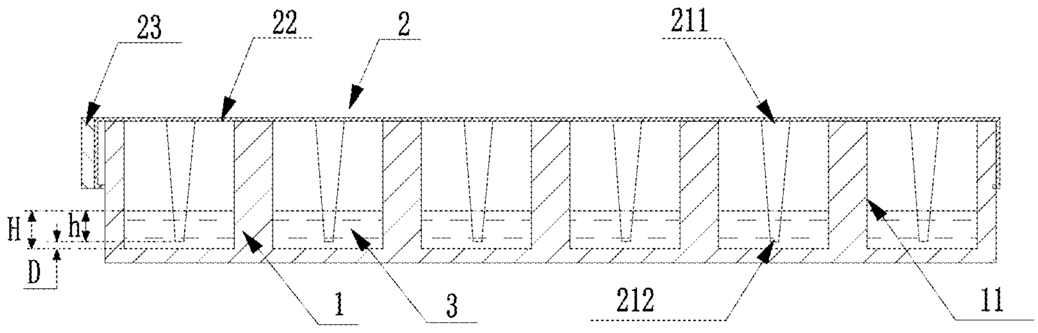
FIG. 2*c* is a schematic diagram of a cross-section structure at a position L1-L1 in FIG. 2*a*.

In an exemplary embodiment, as shown in FIG. 2*c*, a depth H of the culture solution 3 may be 1 mm to 4 mm, a depth h of the vibration member 21 extending into the culture solution 3 of the corresponding accommodating structure 11 is 0.5 mm to 3 mm, and a distance D between the vibration member 21 and a bottom of the accommodating structure 11 is 0.5 mm to 1.5 mm. For example, the depth H of the culture solution is 2 mm to 3 mm, the depth h of the vibration member 21 extending into the culture solution 3 of the corresponding accommodating structure 11 is 1 mm to 2 mm, and the distance D between the vibration member 21 and the bottom of the accommodating structure 11 is 1 mm.

In an exemplary embodiment, as shown in FIGS. 2, 5, 7, 9 and 11, an orthographic projections of the plurality of vibration members 21 on the culture plate 1 are within a range of orthographic projections of the plurality of accommodating structures 11 on the culture plate.

In an exemplary embodiment, in the structure shown in FIGS. 2, 5, 7, 9 and 11, an area of the orthographic projection of the vibration member 21 on the culture plate 1 is 30% to 70% of an area of the orthographic projection of the accommodating structure 11 corresponding to the vibration member 21 on the culture plate. In an embodiment of the present disclosure, when designing a relationship between the area of the orthographic projection of the vibration member 21 on the culture plate and the area of the orthographic projection of the accommodating structure on the culture plate, on the one hand, it is necessary to consider that the bonding stability between the vibration member 21 and the cover plate is low in a case that the area of the orthographic projection of the vibration member 21 on the culture plate 1 occupies a small part of the area of the orthographic projection of the accommodating structure 11 on the culture plate 1; on the other hand, it is necessary to consider that in a case that the area of the orthographic projection of the vibration member 21 on the culture plate 1 occupies a large part of the area of the orthographic projection of the accommodating structure 11 on the culture plate 1, the functional effect of the culture structure will be reduced due to the vibration resistance caused by the increase of the mass of the vibration member 21. In an embodiment of the present disclosure, since the area of the orthographic projection of the vibration member 21 on the culture plate 1 is 30% to 70% of the area of the orthographic projection of the accommodating structure 11 corresponding to the vibration member 21 on the culture plate, on the one hand, the bonding between the vibration member 21 and the cover plate 22 may be relatively stable; on the other hand, the mass of the vibration member 21 is appropriate, and the vibration resistance may not affect the functional effect of the culture structure.

In an exemplary embodiment, as shown in FIG. 2, the vibration member 21 may be a vertebral structure, and an area of the orthographic projection of the first end 211 of the vibration member 21 on the cover plate 22 is larger than an area of the orthographic projection of the second end 212 of the vibration member 21 on the cover plate 22. In an embodiment of the present disclosure, the vibration member 21 in the culture structure is provided as a vertebral structure, and may cooperate with the large-size culture plate 1 to carry out a rotational movement of the particles. In other embodiments, the vibration member 21 may be a column structure, a cuboid structure, etc. For example, the vibration member 21 in the embodiments shown in FIGS. 5 and 7 is a column structure, and the vibration member 21 in the embodiments shown in FIGS. 9 and 11 is a cuboid structure.

Figure 2D:
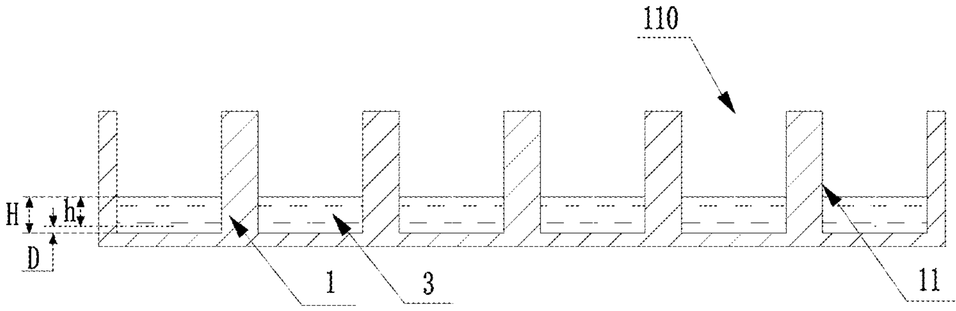
FIG. 2*d* is a schematic diagram of a cross-section structure of a culture plate in the culture structure shown in FIG. 2*a*.
Figure 3:
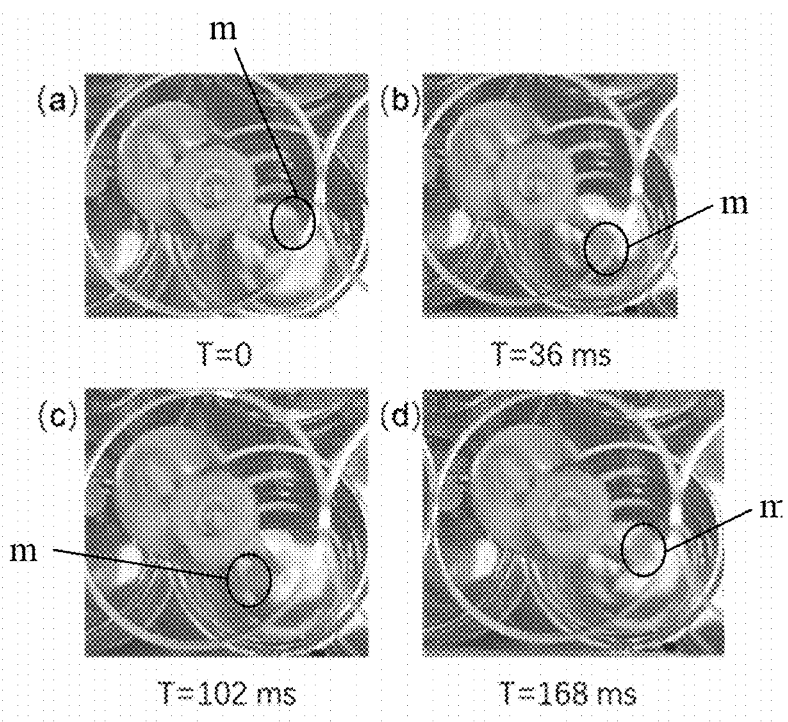
FIG. 3 is a schematic diagram of a movement trajectory of particles in an accommodating structure in a culture structure according to an exemplary embodiment of the present disclosure.
Figure 4A:
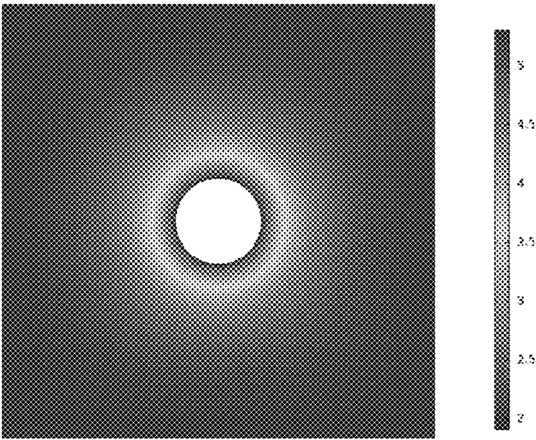
FIG. 4*a* is a schematic diagram of a simulation result of an acoustic pressure field of a culture structure according to an exemplary embodiment of the present disclosure.
Figure 4B:
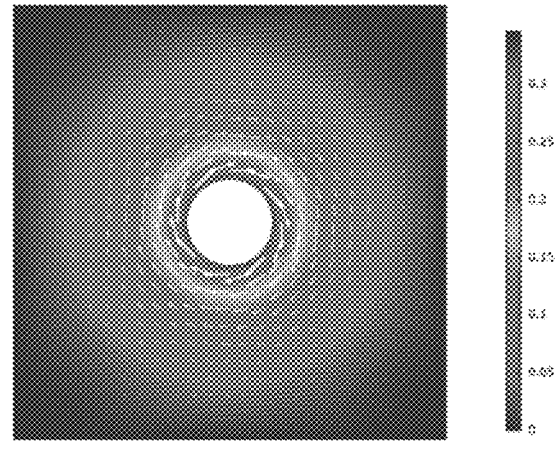
FIG. 4*b* is a schematic diagram of a simulation result of an acoustic flow field of a culture structure according to an exemplary embodiment of the present disclosure.

In an exemplary embodiment, as shown in FIG. 2, end faces of the first end 211 and the second end 212 of the vibration member 21 are both circular, a diameter of the end face of the first end 211 of the vibration member 21 is 0.4 mm to 0.8 mm, a diameter of the end face of the second end 212 of the vibration member 21 is 0.1 mm to 0.3 mm, and the accommodating structure 11 is a hollow cylindrical structure with an inner diameter of 14 mm to 18 mm. For example, in the culture structure shown in FIG. 2, the diameter of the end face of the first end 211 of the vibration member 21 is 0.6 mm, the diameter of the end face of the second end 212 is 0.2 mm, the inner diameter of the accommodating structure of the hollow cylindrical structure is 16 mm. A 0.5 V voltage signal with a frequency of 34 kHz is applied to two orthogonal piezoelectric transducers 231 of the culture structure shown in FIG. 2, the phase difference between the two orthogonal piezoelectric transducers is set to 90°, the culture solution 3 in the accommodating structure 11 flows rapidly, and the particles with a diameter of 3 mm rotate on their own axis rapidly near the vibration member 21 or around the vibration member 21. FIG. 3 is a schematic diagram of movement trajectory of particles with a diameter of 3 mm around the vibration member 21 (m is a particle of 3 mm, and FIGS. 3*a* to 3*d* show the positions of node particles m at time nodes 0 millisecond, 36 millisecond, 102 millisecond and 168 millisecond, respectively). FIG. 4*a* is a schematic diagram of a simulation effect of an acoustic field of an accommodating structure, where the unit is Mpa. As shown in FIG. 4*a*, the closer the region to the vibration member 21, the stronger the acoustic field; and the maximum acoustic field intensity is reached at the surface of the vibration member 21. FIG. 4*b* is a schematic diagram of a simulation effect of an acoustic flow field in an accommodating structure, where the unit is mm/S. The closer the region to the vibration member 21, the stronger the acoustic flow; and the maximum acoustic flow is reached at an outer surface of the vibration member. As can be seen from FIGS. 3 and 4, the particles with a diameter of 3 mm finally rotate on their own axis rapidly or rotate around the column near the vibration member 21, and the particles in the culture solution may realize active periodic movement, thereby solving the death problem caused by lack of oxygen.

In an exemplary embodiment, in the culture structure shown in FIG. 2, diameters of end faces of the first ends 211 and the second ends 212 of the plurality of vibration members 21 may be arranged to gradually decrease from being close to the piezoelectric transducer 231 to being far away from the piezoelectric transducer 231. For example, in FIG. 2, the diameter of the end face of the first end 211 of the vibration member 21 closest to the piezoelectric transducer 231 may be set to 0.6 mm, and the diameter of the end face of the second end 212 may be set to 0.3 mm. The diameter of the end face of the first end 211 of the vibration member 21 furthest from the piezoelectric transducer 231 may be set to 0.4 mm, and the diameter of the end face of the second end 212 may be set to 0.1 mm. The vibration signal generated by the piezoelectric transducer 231 generally has some loss during propagation with the distance increasing. The diameter of the end face of the vibration member 21 which is further away from the piezoelectric transducer 231 is relatively small (the vibration resistance is relatively small), and the diameter of the end face of the vibration member 21 which is close to the piezoelectric transducer 231 is relatively large (the vibration resistance is relatively large). Therefore, the difference in the movements of the culture solution driven by the vibration member 21 at different distances due to the loss of the vibration signal may be compensated as much as possible, so that the plurality of vibration members 21 drive the culture solution in the accommodating structure 11 to produce the same movement as far as possible according to the vibration signal.

In an exemplary embodiment, as shown in FIGS. 5 and 7, the vibration member 21 has a column structure and end faces of the first end 211 and the second end 212 of the column structure are both circular.

In an exemplary embodiment, in the structure shown in FIG. 5, the diameters of end faces of the first end 211 and the second end 212 of the column structure are 0.1 mm to 6 mm. The accommodating structure 11 is a hollow cylindrical structure with an inner diameter of 0.5 mm to 26 mm. An orthographic projection of the vibration member 21 of the column structure on the cover plate 22 falls within a range of an orthographic projection of the accommodating structure 11 on the cover plate 22.

In an exemplary embodiment, as shown in FIG. 5, the diameters of end faces of the first end 211 and the second end 212 of the vibration member 21 of the column structure are 0.1 mm to 0.4 mm. The inner diameter of the accommodating structure 11 of the hollow cylindrical structure is 0.5 mm to 1.5 mm.

For example, in the embodiment shown in FIG. 5, the vibration member 21 is provided as a cylindrical column structure, the diameter of the end face of the first end 211 of the column structure is 0.2 mm, and the accommodating structure 11 is provided as a hollow cylindrical structure having a diameter of 1 mm. A 0.5 V voltage signal with a frequency of 30 kHz is applied to two orthogonal piezoelectric transducers 231 of the culture structure shown in FIG. 5. The phase difference between the two orthogonal piezoelectric transducers 231 is set to 90°. Simulation is performed for the structure shown in FIG. 5. FIG. 6*a* shows a schematic diagram of a simulation effect of an acoustic field of an accommodating structure, where the unit is Mpa. As shown in FIG. 6*a*, the closer the region to the vibration member 21 of the column structure, the stronger the acoustic field; and the maximum acoustic field intensity is reached at the outer surface of the vibration member. FIG. 6*b* is a schematic diagram of a simulation effect of an acoustic flow field in an accommodating structure, wherein the unit is mm/S. The closer the region to the vibration member 21 of the column structure, the stronger the acoustic flow; and the maximum acoustic flow is reached at the outer surface of the vibration member. FIG. 6*c* is a schematic diagram of a simulation result of particle tracking trajectories of particles of 500 μm in an accommodating structure, where the unit is μm/S. From the simulation result in FIG. 6, it can be seen that particles having a diameter of 500 μm may rotate to a center of the region of the accommodating structure 11 (the periphery of the vibration member 21) within 300 s, and then stop moving when being attached to the vibration member 21 (the particles may be attached to the periphery of the vibration member 21 to vibrate).

In the culture structure shown in FIG. 5, the vibration member 21 is provided as a column structure, so as to adsorb small-sized particles quickly in a small range, and realize the aggregation of particles. Compared with the culture structure shown in FIG. 2 in which the vibration member 21 is provided as a vertebral structure, the culture structure shown in FIG. 5 achieves different technical effects.

In an exemplary embodiment, in the culture structure shown in FIG. 5, the diameters of the end faces of the first end 211 and the second end 212 of the plurality of vibration members 21 may be arranged to gradually decrease from being close to the piezoelectric transducer 231 to being far away from the piezoelectric transducer 231. For example, the diameters of the end faces of the first end 211 and the second end 212 of the vibration member 21 closest to the piezoelectric transducer 231 in FIG. 5 may be set to 0.4 mm; and the diameters of the end faces of the first end 211 and the second end 212 of the vibration member 21 farthest from the piezoelectric transducer 231 may be set to 0.1 mm. The vibration signal generated by the piezoelectric transducer 231 generally has some loss during propagation with the distance increasing. The diameter of the end face of the vibration member 21 which is further away from the piezoelectric transducer 231 is relatively small (the vibration resistance is relatively small), and the diameter of the end face of the vibration member 21 which is close to the piezoelectric transducer 231 is relatively large (the vibration resistance is relatively large). Therefore, the difference in the movements of the culture solution driven by the vibration member 21 at different distances due to the loss of the vibration signal may be compensated as much as possible, so that the plurality of vibration members 21 drive the culture solution in the accommodating structure 11 to produce the same movement as far as possible according to the vibration signal.

In another exemplary embodiment, in the culture structure shown in FIG. 5, the accommodating structure 11 may be provided as a hollow cuboid structure, an opening 110 position of the accommodating structure 11 of the hollow cuboid structure is square, a side length of the square opening 110 position may be set to 0.5 mm to 1.5 mm, and the diameters of the end faces of the first end 211 and the second end 212 of the vibration member 21 of the column structure may be set to 0.1 mm to 0.4 mm.

In an exemplary embodiment, as shown in FIG. 7, the diameters of the end faces of the first end 211 and the second end 212 of the column structure are 0.1 mm to 6 mm, the accommodating structure 11 is a hollow cuboid structure, the opening 110 position of the accommodating structure 11 of the hollow cuboid structure is square, the side length of the square opening 110 position is 0.5 mm to 26 mm, and a plane where the opening 110 position is located is parallel to a plane where the cover plate 22 is located; an orthographic projection of the vibration member 21 of the column structure on the cover plate 22 falls within a range of an orthographic projection of the accommodating structure 11 on the cover plate 22.

In an exemplary embodiment, as shown in FIG. 7, the diameters of the end faces of the first end 211 and the second end 212 of the vibration member 21 of the column structure are 0.1 mm to 0.4 mm; and the side length of the square opening position is 0.5 mm to 1.5 mm. For example, the accommodating structure 11 in the embodiment shown in FIG. 7 is provided as a hollow cuboid structure and the side length of the square opening 110 position of the accommodating structure 11 is a value between 0.5 mm and 1.5 mm. In an exemplary embodiment, in the culture structure shown in FIG. 7, the diameters of the end faces of the first end 211 and the second end 212 of the plurality of vibration members 21 may be arranged to gradually decrease from being close to the piezoelectric transducer 231 to being far away from the piezoelectric transducer 231. For example, the diameters of the end faces of the first end 211 and the second end 212 of the vibration member 21 closest to the piezoelectric transducer 231 in FIG. 7 may be set to 0.4 mm; and the diameters of the end faces of the first end 211 and the second end 212 of the vibration member 21 farthest from the piezoelectric transducer 231 may be set to 0.1 mm. The vibration signal generated by the piezoelectric transducer 231 generally has some loss during propagation with the distance increasing. The diameter of the end face of the vibration member 21 which is further away from the piezoelectric transducer 231 is relatively small (the vibration resistance is relatively small), and the diameter of the end face of the vibration member 21 which is close to the piezoelectric transducer 231 is relatively large (the vibration resistance is relatively large). Therefore, the difference in the movements of the culture solution driven by the vibration member 21 at different distances due to the loss of the vibration signal may be compensated as much as possible, so that the plurality of vibration members 21 drive the culture solution in the accommodating structure 11 to produce the same movement as far as possible according to the vibration signal.

In another exemplary embodiment, as shown in FIG. 7, the diameters of the end faces of the first end 211 and the second end 212 of the vibration member 21 of the column structure may be 1 mm to 6 mm; and the side length of the square opening position is 10 mm to 26 mm. In an exemplary embodiment, in the culture structure shown in FIG. 7, the diameters of the end faces of the first end 211 and the second end 212 of the plurality of vibration members 21 may be arranged to gradually decrease from being close to the piezoelectric transducer 231 to being far away from the piezoelectric transducer 231. For example, the diameters of the end faces of the first end 211 and the second end 212 of the vibration member 21 closest to the piezoelectric transducer 231 in FIG. 7 may be set to 6 mm; and the diameters of the end faces of the first end 211 and the second end 212 of the vibration member 21 farthest from the piezoelectric transducer 231 may be set to 1 mm. The vibration signal generated by the piezoelectric transducer 231 generally has some loss during propagation with the distance increasing. The diameter of the end face of the vibration member 21 which is further away from the piezoelectric transducer 231 is relatively small (the vibration resistance is relatively small), and the diameter of the end face of the vibration member 21 which is close to the piezoelectric transducer 231 is relatively large (the vibration resistance is relatively large). Therefore, the difference in the movements of the culture solution driven by the vibration member 21 at different distances due to the loss of the vibration signal may be compensated as much as possible, so that the plurality of vibration members 21 drive the culture solution in the accommodating structure 11 to produce the same movement as far as possible according to the vibration signal.

For example, in the embodiment shown in FIG. 7, the vibration member 21 is provided as a cylindrical column structure, the diameters of the end faces of the first end 211 and the second end 212 of the column structure is set to 3 mm, the accommodating structure 11 is provided as a hollow cuboid structure, and the side length of the square opening 110 position of the hollow cuboid structure is 18 mm.

In another exemplary embodiment, the accommodating structure 11 in the embodiment shown in FIG. 7 may be provided as a hollow cylindrical structure, and the diameters of the end faces of the hollow cylinder may be set to a value between 10 mm and 26 mm.

In an exemplary embodiment, in the culture structure shown in FIG. 7, the piezoelectric transducer 231 has an input voltage signal of 0.3 V to 0.8 V, the frequency of the input voltage signal is 25 kHz to 35 kHz, and the phase difference between the vibration signals generated by the two piezoelectric transducers is −10° to 10°. For example, in the culture structure shown in FIG. 7, two piezoelectric transducers are orthogonal, the phase difference of vibration signals generated by the two piezoelectric transducers 231 is 0°, the input voltage signal of the piezoelectric transducer 231 is 0.5 V, and the frequency of the input voltage signal is 30 KHz. FIG. 8 is schematic diagrams of simulation results of the culture structure described in FIG. 7. The simulation results shown in FIG. 8 correspond to the parameters of the culture structure of FIG. 7 as follows: the diameters of the end faces of the first end 211 and the second end 212 of the vibration member 21 of the column structure are 3 mm, the accommodating structure 11 is a hollow cuboid structure, the side length of the square opening 110 position of the hollow cuboid structure is 18 mm; in the culture structure, two piezoelectric transducers are orthogonal, the phase difference of vibration signals generated by the two piezoelectric transducers 231 is 0°, the input voltage signal of the piezoelectric transducer 231 is 0.5 V, the frequency of the input voltage signal is 30 kHz, and the particle diameter in the culture solution is 4 mm. FIG. 8 shows schematic diagrams of simulation results. Particles of about 4 mm may be concentrated to two ends of the cylindrical structure of the vibration member 21 extending to the culture solution 3 in the circumferential direction in about 300 seconds (i.e., the two positions of particle concentration are located on the surface of the cylindrical structure extending to the culture solution, and the positions of particle concentration are symmetrical with respect to a center line of the vibration member 21), and then no relative motion is made (the particles may vibrate under the drive of the vibration member 21). FIG. 8*a* is a schematic diagram of a simulation effect of an acoustic pressure field, where the unit is MPa; FIG. 8*b* is a schematic diagram of a simulation effect of an acoustic flow, where the unit is millimeter/second; and FIG. 8*c* is a schematic diagram of particle tracking trajectories, where the unit is microns/second. According to the simulation results of FIG. 8, it can be seen that the culture structure shown in FIG. 7 may realize the concentration of particles scattered in a large area of culture solution.

In an exemplary embodiment, as shown in FIG. 9, the vibration member 21 may be a cuboid structure, the accommodating structure 11 may be a hollow cuboid structure, and an orthographic projection of the accommodating structure 11 on the cover plate 22 covers an orthographic projection of the vibration member 21 on the cover plate 22.

In an exemplary embodiment, as shown in FIG. 9, end faces of the first end 211 and the second end 212 of the vibration member 21 of the cuboid structure are both square, and a side length of the square is 4 mm to 12 mm. An opening position of the accommodating structure 11 is square, a side length of the square opening position is 14 mm to 22 mm, and a plane where the opening position is located is parallel to a plane where the cover plate is located. In the structure shown in FIG. 9, four sides of the end faces of the first end 211 and the second end 212 are parallel to four sides of the opening position of the accommodating structure 11, respectively.

For example, in the embodiment shown in FIG. 9, the vibration member 21 is provided as a cuboid structure, and end faces of the first end 211 and the second end 212 of the cuboid structure are both square with a side length of 8 mm; and the accommodating structure 11 is provided as a hollow cuboid structure, an opening position of the hollow cuboid structure is square with a side length of 18 mm. The culture structure shown in FIG. 9 may be used for extracting particles from liquid samples and dividing the particles in the culture solution into four equal parts. A 0.5 V voltage signal with a frequency of 30 kHz is applied to two orthogonal piezoelectric transducers 231 of the culture structure shown in FIG. 9, the phase difference between the two orthogonal piezoelectric transducers 231 is set to 90°, and particles of the culture solution are 2 mm. FIG. 10 are schematic diagrams of simulation results of an accommodating structure in FIG. 9. According to the simulation results, the particles with a diameter of 2 mm may move quickly and evenly to the four outer side wall surfaces of the vibration member 21 in 40 s, so as to realize the adsorption of particles in liquid, which may be used for extracting particles from liquid samples and dividing them into four equal parts, or may play a role as a cell counting plate.

In an exemplary embodiment, in the structure shown in FIG. 9, side lengths of the end faces of the first ends and the second ends of the plurality of vibration members 21 gradually decrease from being close to the piezoelectric transducer 231 to being far away from the piezoelectric transducer 231. For example, in FIG. 9, the side lengths of the end faces of the first end 211 and the second end 212 of the vibration member 21 closest to the piezoelectric transducer 231 may be set to 10 mm; and the side lengths of the end faces of the first end 211 and the second end 212 of the vibration member 21 farthest from the piezoelectric transducer 231 may be set to 5 mm. The vibration signal generated by the piezoelectric transducer 231 generally has some loss during propagation with the distance increasing. The side length of the end face of the vibration member 21 which is further away from the piezoelectric transducer 231 is relatively small (the vibration resistance is relatively small), and the side length of the end face of the vibration member 21 which is close to the piezoelectric transducer 231 is relatively large (the vibration resistance is relatively large). Therefore, the difference in the movements of the culture solution driven by the vibration member 21 at different distances due to the loss of the vibration signal may be compensated as much as possible, so that the plurality of vibration members 21 drive the culture solution in the accommodating structure 11 to produce the same movement as far as possible according to the vibration signal.

In an exemplary embodiment, as shown in FIG. 11, the vibration member 21 may be a column structure, the end faces of the first end 211 and the second end 212 of the column structure are circular, and any one of the accommodating structures 11 is corresponding to two column structures, and orthographic projections of the two column structures on the cover plate 22 are within a range of an orthographic projection of the corresponding accommodating structure 11 on the cover plate 22

In an exemplary embodiment, in the culture structure shown in FIG. 11, the diameters of the end faces of the first end 211 and the second end 212 of the vibration member 21 of the column structure are 0.1 mm to 0.4 mm, and a spacing R between the two vibration members 21 corresponding to the same accommodating structure 11 is 0.1 mm to 0.3 mm. The accommodating structure 11 may be a hollow cylindrical structure having an inner diameter of 1.1 mm to 3.2 mm. Alternatively, the accommodating structure 11 may be a hollow cuboid structure, an opening position of the accommodating structure 11 is square, a side length of the square opening position is 1.1 mm to 3.2 mm, and a plane where the opening position is located is parallel to a plane where the cover plate 22 is located.

For example, the accommodating structure 11 of the culture structure shown in FIG. 11 is a hollow cuboid structure, the opening position of the hollow cuboid structure is square, the side length of the square opening position is 2 mm, and the plane where the opening position is located is parallel to the plane where the cover plate 22 is located. The accommodating structure 11 is corresponding to two vibration members 21 of a cylindrical column structure, the diameter of the end face of each vibration member 21 is 0.2 mm, and the spacing between the two vibration members 21 corresponding to the same accommodating structure 11 is 0.2 mm. A 0.5 V voltage signal with a frequency of 30 kHz is applied to two orthogonal piezoelectric transducers 231 of the organoid structure shown in FIG. 11. The phase difference between the two orthogonal piezoelectric transducers 231 is set to 90°. The particles in the culture solution are of about 1 mm. The simulation results are shown in FIG. 12. The particles with a diameter of 1 mm rotate through the entire fluid region within 2000 s and finally concentrate on the two vibration members 21 of a column structure. Under the action of the vibration members 21, they are fully moved and stirred in the whole coating liquid and finally taken out directly on the vibration members 21.

In an exemplary embodiment, in the culture structure shown in FIG. 11, the diameters of the end faces of the first ends 211 and the second ends 212 of the plurality of vibration members 21 may be arranged to gradually decrease from being close to the piezoelectric transducer 231 to being far away from the piezoelectric transducer 231. For example, the diameters of the end faces of the first end 211 and the second end 212 of the vibration member 21 closest to the piezoelectric transducer 231 in FIG. 11 may be set to 0.2 mm; and the diameters of the end faces of the first end 211 and the second end 212 of the vibration member 21 farthest from the piezoelectric transducer 231 may be set to 0.1 mm. The vibration signal generated by the piezoelectric transducer 231 generally has some loss during propagation with the distance increasing. The diameter of the end face of the vibration member 21 which is further away from the piezoelectric transducer 231 is relatively small (the vibration resistance is relatively small), and the diameter of the end face of the vibration member 21 which is close to the piezoelectric transducer 231 is relatively large (the vibration resistance is relatively large). Therefore, the difference in the movements of the culture solution driven by the vibration member 21 at different distances due to the loss of the vibration signal may be compensated as much as possible, so that the plurality of vibration members 21 drive the culture solution in the accommodating structure 11 to produce the same movement as far as possible according to the vibration signal.

In an exemplary embodiment, the vibration signal generating structure 23 may include a plurality of piezoelectric transducers, the vibration members 21 may be located at a position where a bottom of the culture plate 1 is corresponding to the plurality of accommodating structures 11, respectively, the plurality of piezoelectric transducers are respectively corresponding to the plurality of vibration members, and a vibration signal generated by each piezoelectric transducer is applied to the corresponding vibration member. In an exemplary embodiment, the piezoelectric transducer may be an annular piezoelectric transducer. An orthographic projection of the piezoelectric transducer on the cover plate 21 is at least partially overlapped with an orthographic projection of the corresponding vibration member 21 on the cover plate 22.

In an exemplary embodiment, in the structure shown in FIGS. 2, 5, 7, 9 and 11, the thickness of the culture plate 1 may be 15 mm to 21 mm, and the height of the vibration member 21 may be 14 mm to 20 mm. For example, the thickness of the culture plate 1 may be 18 mm and the height of the vibration member 21 may be 17 mm.

A plurality of classes of culture structures provided by embodiments of the present disclosure will be described below with reference to the accompanying drawings.

FIG. 1 is a schematic diagram of a three-dimensional structure of a culture structure according to an embodiment of the present disclosure. FIG. 2*a* is a schematic diagram of a planar structure of a culture structure viewed on the side of a cover plate. FIG. 2*b* is a schematic diagram of a planar structure of a culture structure shown in FIG. 2*a* with a cover plate removed. FIG. 2*c* is a schematic diagram of a cross-section structure of the culture structure shown in FIG. 2*a* along the position L1-L1. FIG. 2*d* is a schematic diagram of a cross-section structure of the culture plate 1.

As shown in FIGS. 1 and 2*a*-2*c*, the culture structure includes a culture plate 1 and a vibration structure 2 arranged above the culture plate 1, a plurality of accommodating structures 11 are provided on the culture plate 1, the plurality of accommodating structures 11 accommodate culture solution 3 inside, the vibration structure 2 includes a vibration member 21, a cover plate 22 and a vibration signal generating structure 23, and the plurality of vibration structures 21 are arranged corresponding to the plurality of accommodating structures 11. In the culture structure shown in FIGS. 2*a*-2*d*, the vibration member 21 is a vertebral structure, the accommodating structure 11 may be a hollow cylindrical structure, and the plurality of accommodating structures 11 of hollow cylindrical structures are arranged corresponding to the plurality of vibration members 21 of vertebral structures.

In the embodiment shown in FIG. 2, the vibration signal generating structure 23 is provided with two piezoelectric transducers 231 arranged at two adjacent edges of the cover plate 22, and the cover plate shown in FIG. 2 is rectangular so that propagation directions of vibration signals generated by the two piezoelectric transducers are orthogonal in a plane where the cover plate 22 is located. Since the selected acoustic wave frequency in the embodiments of the present disclosure is below 100 kHz, the corresponding acoustic wavelength in the device is on the order of centimeters, and the bulk acoustic wave is generated within several periods without obvious additive effect, the size and shape of the selected transducers do not have a decisive influence on the result, and their orthogonal position directly determines the flow result.

The vibration member 21 of vertebral structure shown in FIG. 2*c* includes a first end 211 and a second end 212 arranged oppositely, the first end 211 of the vibration member 21 is connected to the cover plate 22, and the second end 212 of the vibration member 21 extends away from the cover plate 22 into the culture solution 3 of the corresponding accommodating structure 11 and is not in contact with the accommodating structure 11 and the culture plate 1. The height of the selected vibration member 21 is mainly restricted by the depth of the liquid driven by the acoustic flow field. Considering the size of the vibration member 21, the depth of the liquid which flows obviously under the action of the acoustic flow field is on the order of millimeters, so that the height of the selected vibration member 21 is a height close to the bottom of the accommodating structure 11, but the second end 212 of the vibration member 21 is not in contact with the accommodating structure 11 and the culture plate 1. In an exemplary embodiment, the depth H of the culture solution 3 may be 1 mm to 4 mm, the depth h of the vibration member 21 extending into the culture solution 3 of the corresponding accommodating structure 11 may be 0.5 mm to 3 mm, and the distance D between the vibration member 21 and the bottom of the accommodating structure 11 may be 0.5 mm to 1.5 mm.

The connection between the piezoelectric transducer 231 and the cover plate 22, and between the cover plate 22 and the vibration member 21 in the embodiments of the present disclosure may be realized by at least one of solid hard glass glue, silicone oil, mineral oil, ultrasonic coupling agent and solid glue. On the one hand, the fixation between the two may be realized, and on the other hand, the hard glass glue may reduce acoustic loss during transmission to realize the function to the greatest extent. Thus, in the culture structure shown in FIG. 2*c*, the bulk acoustic waves generated by two orthogonal piezoelectric transducers 231 drive the cover plate 22 coupled thereto to vibrate. The vibration of the cover plate 22 causes a forced vibration of the vertebral structure 213 coupled to its lower surface. When two orthogonal piezoelectric transducers are used to excite with the same input signal, two symmetrical annular acoustic flow fields are generated around the vibration member 21 of vertebral structure, and when two orthogonal piezoelectric transducers are used to excite in a case where the phase difference of the input signal period is a half period, a circular acoustic flow field is generated around the vibration member 21. This acoustic flow field enables the organoid to rotate along the vibration member 21 to realize an active periodic movement, thereby solving the death problem caused by lack of oxygen.

In the embodiment shown in FIG. 2, the diameter of the end face of the first end 211 of the selected vibration member 21 of vertebral structure is set to 0.6 mm, the diameter of the end face of the second end 212 is set to 0.2 mm, the height of the vertebral structure is set to 17 mm, and the accommodating structure 11 is set as a hollow cylindrical structure with a diameter of 16 mm. A signal is applied to two orthogonal piezoelectric transducers 231 of the culture structure, the frequency of the applied signal is 34 kHz, the phase difference of two orthogonal piezoelectric transducers is set to 90°, the input signal is 0.5 V, the amplification factor is 47 dB, the two piezoelectric transducers 231 are started to work, the culture solution 3 in the accommodating structure 11 flows rapidly, and the particles with a diameter of 3 mm rotate on their own axis or rotate around the column rapidly near the vibration member 21. FIG. 3 is a real experimental picture of this embodiment from which it can be seen that particles with a diameter of 3 mm rotate around the vibration member 21. FIG. 4*a* is a diagram of a simulation effect of an acoustic field of an accommodating structure in this embodiment, where the unit is Mpa. It can be seen that the closer the region to the vibration member 21, the stronger the acoustic field, and the maximum acoustic field intensity is reached on the surface of the vibration member 21. FIG. 4*b* is a diagram of a simulation effect of an acoustic flow field of an accommodating structure in this embodiment, where the unit is mm/S. The closer the region to the vibration member 21, the stronger the acoustic flow, and the maximum acoustic flow is reached at the outer surface of the vibration member 21. Therefore, the particles with a diameter of 3 mm finally rotate on their own axis rapidly or rotate around the column near the vibration member 21, and the particles in the culture solution may realize an active periodic movement, thereby solving the death problem caused by lack of oxygen.

Figure 5A:
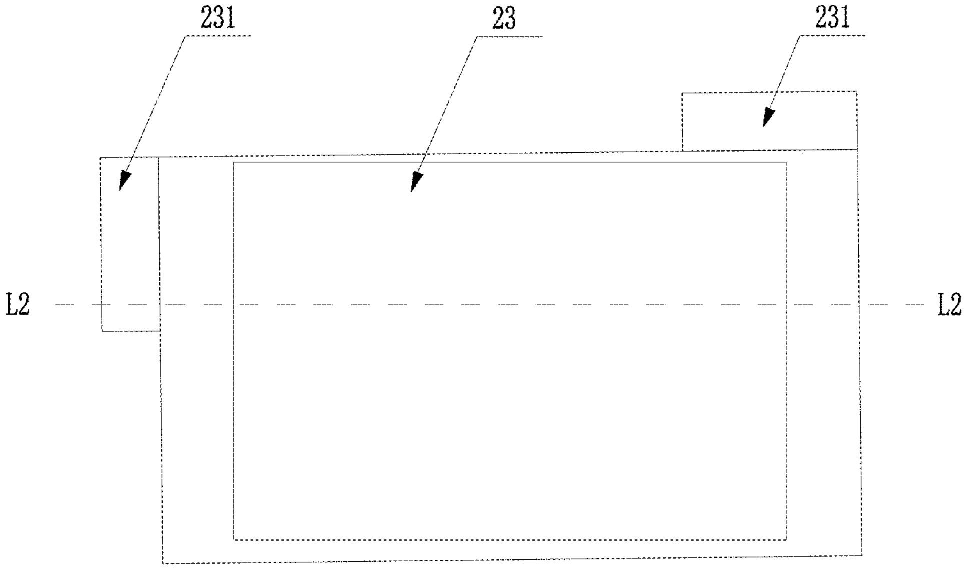
FIG. 5*a* is a schematic diagram of a planar structure of a culture structure according to an embodiment of the present disclosure.
Figure 5B:
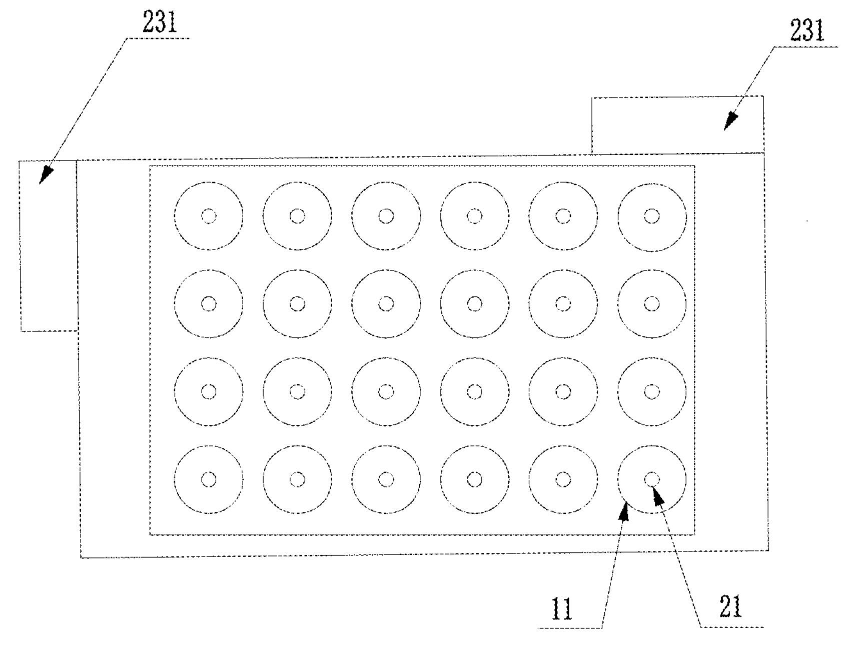
FIG. 5*b* is a schematic diagram of a planar structure of a culture structure shown in FIG. 5*a* with a cover plate removed.
Figure 5C:
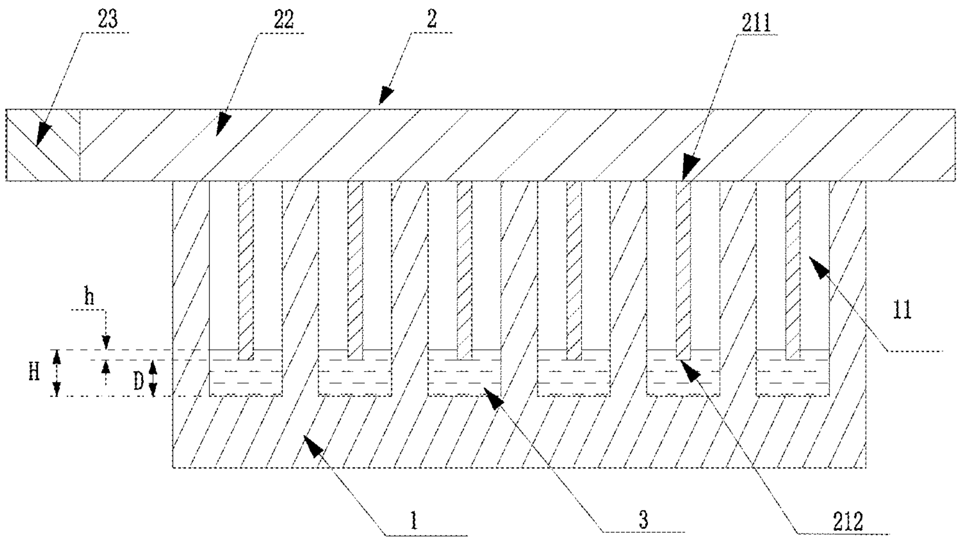
FIG. 5*c* is a schematic diagram of a cross-section structure at a position L2-L2 in FIG. 5*a*.
Figure 6A:
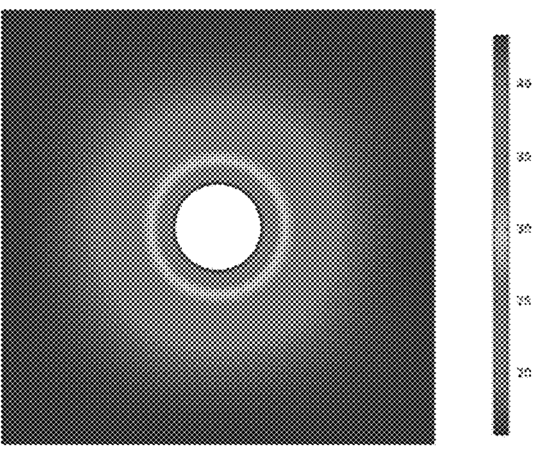
FIG. 6*a* is a schematic diagram of a simulation result of an acoustic pressure field of a culture structure according to an exemplary embodiment of the present disclosure.
Figure 6B:
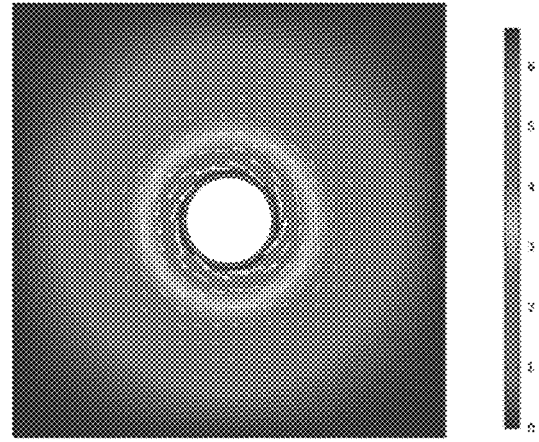
FIG. 6*b* is a schematic diagram of a simulation result of an acoustic flow field of a culture structure according to an exemplary embodiment of the present disclosure.
Figure 6C:
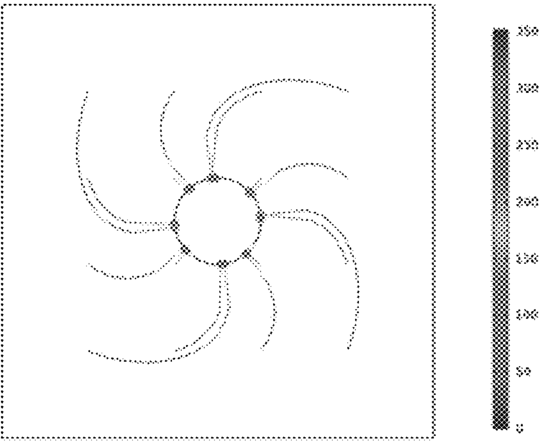
FIG. 6*c* is a schematic diagram of a simulation result of particle tracking trajectories in an acoustic flow field of a culture structure according to an exemplary embodiment of the present disclosure.

FIGS. 5*a*-5*c* are schematic structure diagrams of another culture structure according to an embodiment of the present disclosure. FIG. 5*a* is a schematic diagram of a planar structure of a culture structure on a side of the cover plate; FIG. 5*b* is a schematic diagram of a planar structure of a culture structure shown in FIG. 5*a* with a cover plate removed; and FIG. 5*c* is a schematic diagram of a cross-section structure at a position L2-L2 in FIG. 5*a*.

The culture structure of the embodiment shown in FIGS. 5*a*-5*c* is similar to the culture structure shown in FIGS. 2*a*-2*d* in the basic connecting structure and components, but they are different in the structural shape and size. As shown in FIGS. 5*a*-5*c*, the vibration member 21 is a single cylindrical column structure. The diameter of the selected column structure may be 0.2 mm, and the selected accommodating structure 11 may be a hollow cylindrical structure with an inner diameter of 1 mm. A voltage signal of 0.5 V is applied to the two orthogonal piezoelectric transducers 231 of the culture structure according to this embodiment, the frequency of the applied voltage signal is 30 kHz, and the phase difference between the two orthogonal piezoelectric transducers 231 is set to 90°. Experiments show that the particles with a diameter of 500 μm rotate to the region center of the accommodating structure 11 within 300 s, and then stop moving when being attached to the vibration member 21. FIG. 6*a* is a diagram of a simulation effect of an acoustic field of an accommodating structure in this embodiment, where the unit is Mpa. It can be seen that the closer the region to the vibration member 21, the stronger the acoustic field, and the maximum acoustic field intensity is reached at the outer surface of outside the. FIG. 6*b* is a diagram of a simulation effect of an acoustic flow field of an accommodating structure in this embodiment, where the unit is mm/S. The closer the region to the vibration member 21 of column structure, the stronger the acoustic flow, and the maximum acoustic flow is reached at the outer surface of the vibration member 21. FIG. 6*c* is a schematic diagram of a simulation result of particle tracking trajectories of particles of 500 μm in an accommodating structure of this embodiment, where the unit is μm/S.

In the culture structure shown in FIGS. 2*a* to 2*d*, the vibration member 21 of vertebral structure may cooperate with the large-sized culture plate 1 to carry out the rotational movement of the particles. Compared with the culture structure shown in FIGS. 2*a* to 2*d*, the vibration member 21 in the embodiment shown in FIG. 5 is provided as a column structure, which may quickly adsorb small-sized particles in a small range to realize the aggregation of particles. The two embodiments have different technical effects. Because organs and tissues need to grow together, it is of great significance to realize the aggregation of particles.

Figure 7A:
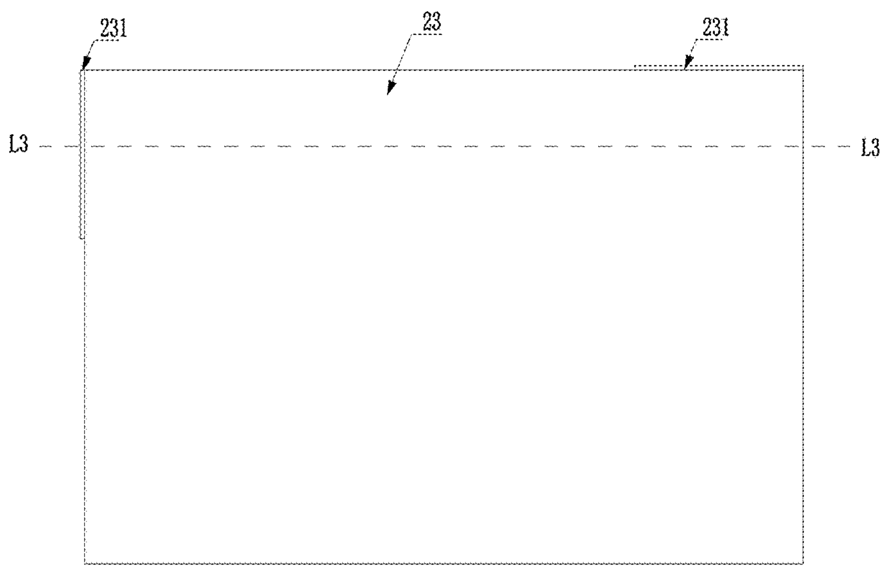
FIG. 7*a* is a schematic diagram of a planar structure of a culture structure according to an exemplary embodiment of the present disclosure.
Figure 7B:
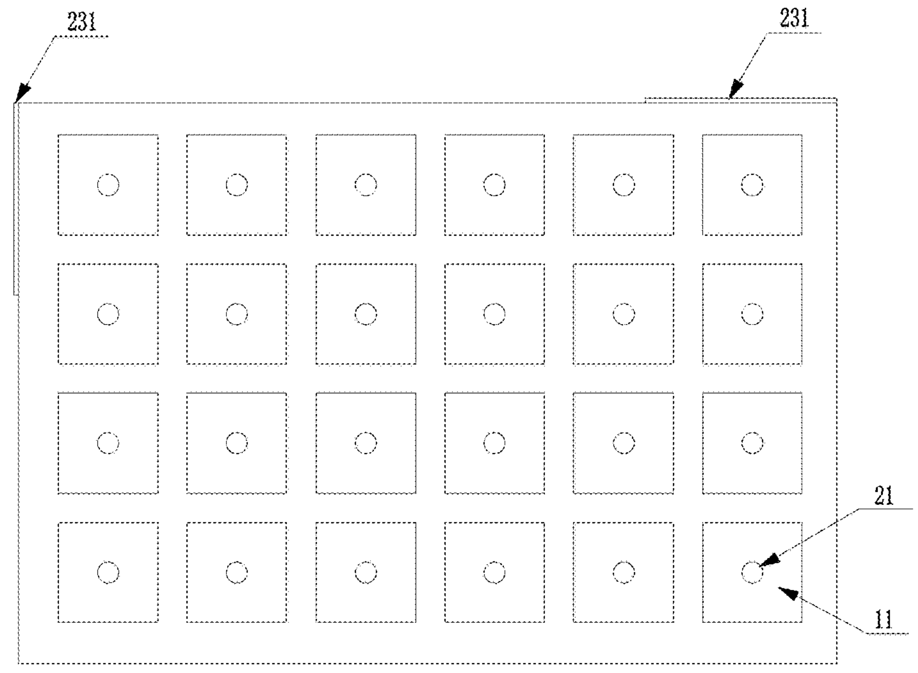
FIG. 7*b* is a schematic diagram of a planar structure of a culture structure shown in FIG. 7*a* with a cover plate removed.
Figure 7C:
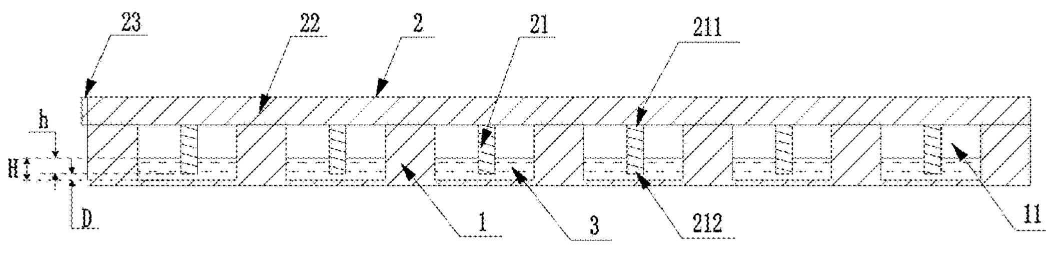
FIG. 7*c* is a schematic diagram of a cross-section structure at a position L3-L3 in FIG. 7*a*.
Figure 8A:
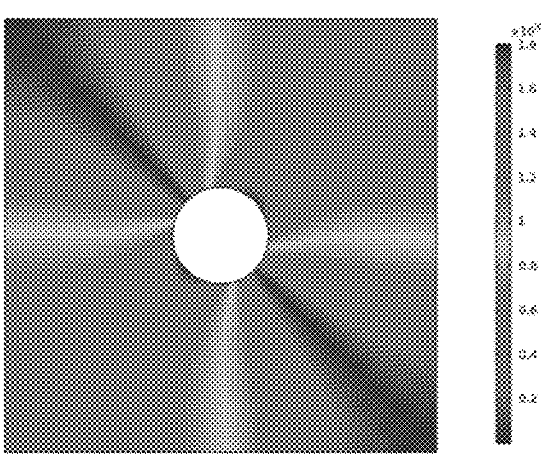
FIG. 8*a* is a schematic diagram of a simulation result of an acoustic pressure field of a culture structure according to an exemplary embodiment of the present disclosure.
Figure 8B:
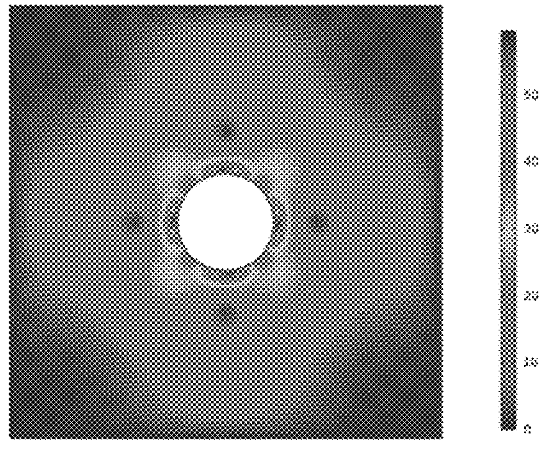
FIG. 8*b* is a schematic diagram of a simulation result of an acoustic flow field of a culture structure according to an exemplary embodiment of the present disclosure.
Figure 8C:
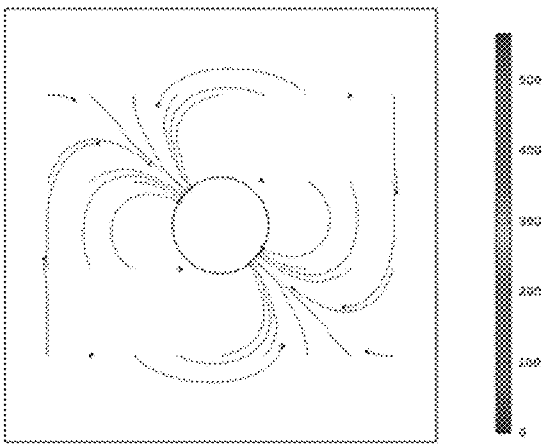
FIG. 8*c* is a schematic diagram of a simulation result of particle tracking trajectories in an acoustic flow field of a culture structure according to an exemplary embodiment of the present disclosure.

The culture structure of the embodiment shown in FIGS. 7*a*-7*c* is similar to the culture structure shown in the above two embodiments in basic connecting structure and components, but they are different in the structural shape and size. As shown in FIGS. 7*a*-7*c*, the vibration member 21 is a single column structure. The selected vibration member 21 of column structure has a diameter of 3 mm. The accommodating structure 11 is provided as a cuboid structure. The opening of the accommodating structure 11 of cuboid structure is square. The side length of the square opening position is 18 mm. A voltage signal of 0.5 V is applied to the two orthogonal piezoelectric transducers 231 of the culture structure described in this embodiment. The frequency of the applied voltage signal is 30 kHz, and the phase difference between the two orthogonal piezoelectric transducers 231 is set to 0°. The experiment shows that the particles with a diameter of 4 mm are concentrated to the region centers of two ends of the vibration member 21 of column structure within 300 s, and then no relative motion is made when being attached to the column structure 214.

FIG. 8*a* is a diagram of a simulation effect of an acoustic field of an accommodating structure 11 in the culture structure shown in FIG. 7, where the unit is Mpa. FIG. 8*b* is a diagram of a simulation effect of an acoustic flow field in an accommodating structure in the culture structure shown in FIG. 7, where the unit is mm/S. FIG. 8*c* is a schematic diagram of a simulation result of particle tracking trajectories of particles of 4 mm in an accommodating structures in the culture structure shown in FIG. 7, where the unit is μm/S.

Compared with the culture structure shown in FIGS. 5A-5*c* which may realize the effect of rotating and concentrating of particles, in the culture structure shown in FIGS. 7*a*-7*c*, the region occupied by the selected accommodating structure 11 on the culture plate 1 has a large square area, and the input signals of the two orthogonal piezoelectric transducers have no phase difference, the functional effect of the acoustic flow field is to perform bipolar capture and concentration, which may realize the concentration of scattered particles in the culture solution region of the accommodating structure with a large area.

Figure 9A:
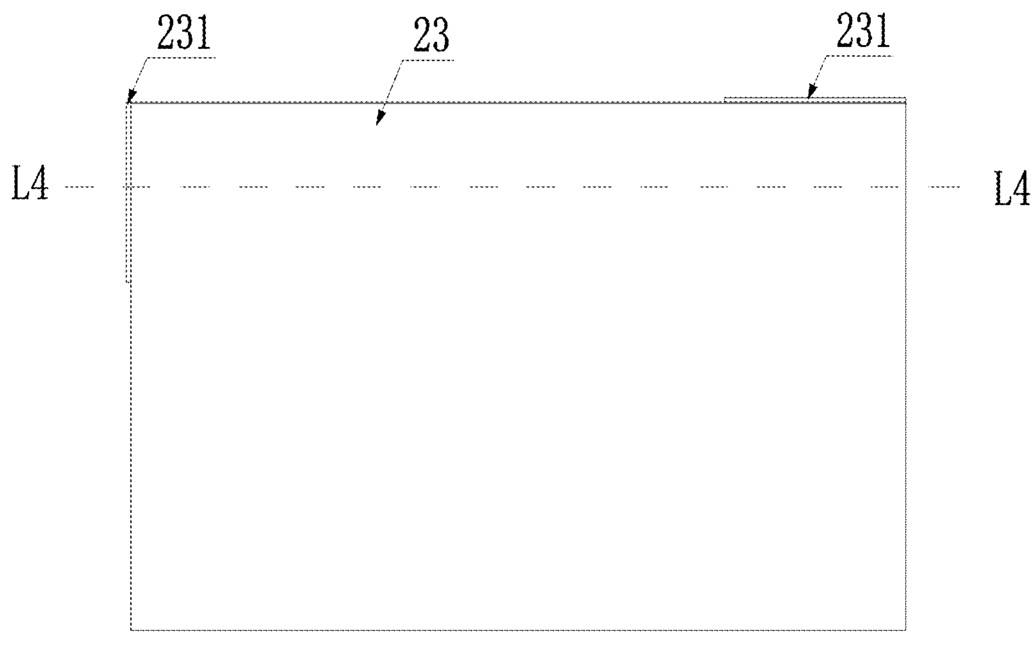
FIG. 9*a* is a schematic diagram of a planar structure of a culture structure according to an exemplary embodiment of the present disclosure.
Figure 9B:
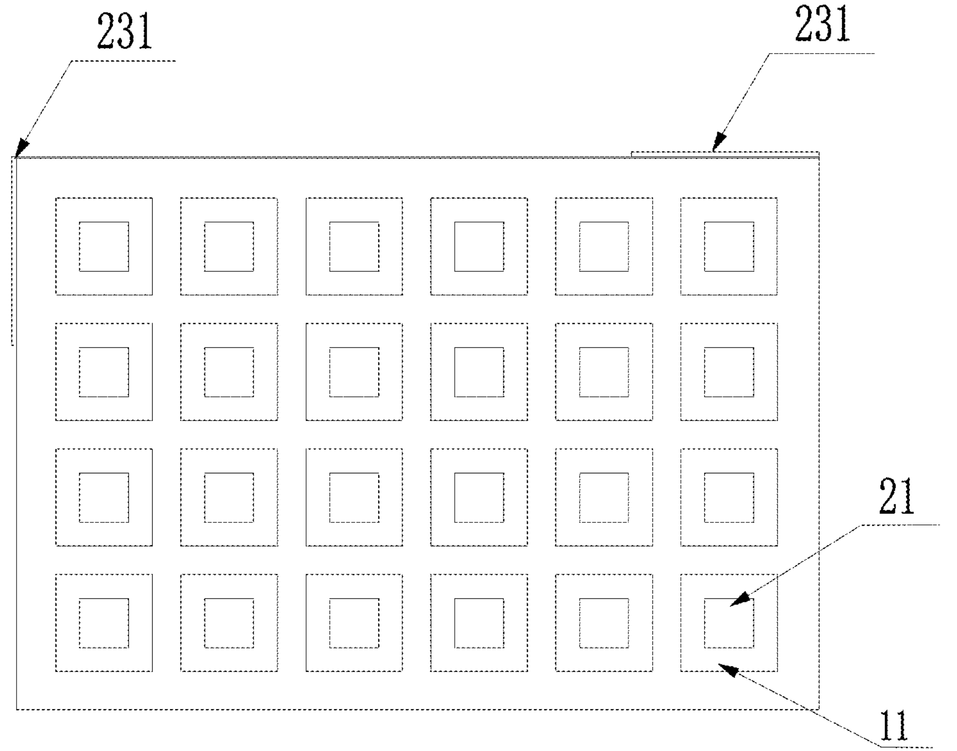
FIG. 9*b* is a schematic diagram of a planar structure of a culture structure shown in FIG. 9*a* with a cover plate removed.
Figure 9C:
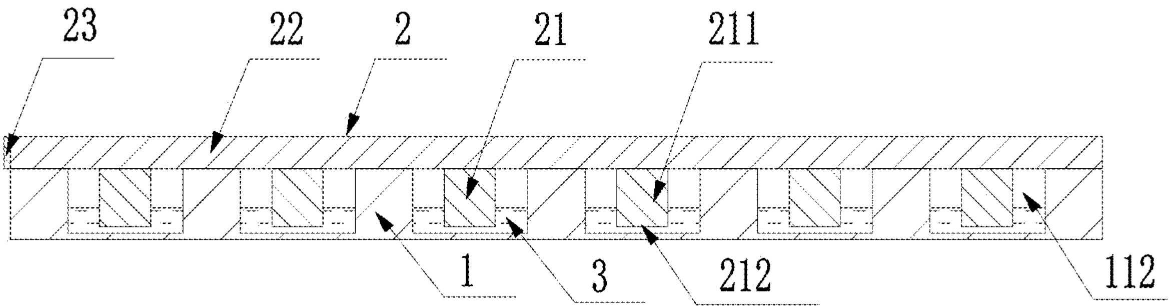
FIG. 9*c* is a schematic diagram of a cross-section structure at a position L4-L4 of the culture structure shown in FIG. 9*a*.

The culture structure of the embodiment shown in FIGS. 9*a*-9*c* is similar to the culture structure shown in the above embodiments in basic connecting structure and components, but they are different in the structural shape and size. As shown in FIGS. 9*b*-9*c*, the vibration member 21 is a cuboid structure. The side length of the end faces of the selected vibration member 21 of cuboid structure is 8 mm, the selected accommodating structure 11 is a hollow cuboid structure, the opening position of the accommodating structure 11 is square, and the side length of the square is 18 mm. A signal is applied to the two orthogonal piezoelectric transducers 231 of the culture structure described in this embodiment, the intensity of the applied signal is 30 kHz, and the phase difference between the two orthogonal piezoelectric transducers 231 is 90°. The experiment shows that the particles with a diameter of 2 mm move quickly and uniformly to the four wall surfaces of the vibration member 21 within 40 seconds, which realizes the adsorption of objects in liquid. Therefore, it may be used for extracting particles from liquid samples and dividing them into four equal parts, or may play a role as a cell counting plate.

Figure 10A:
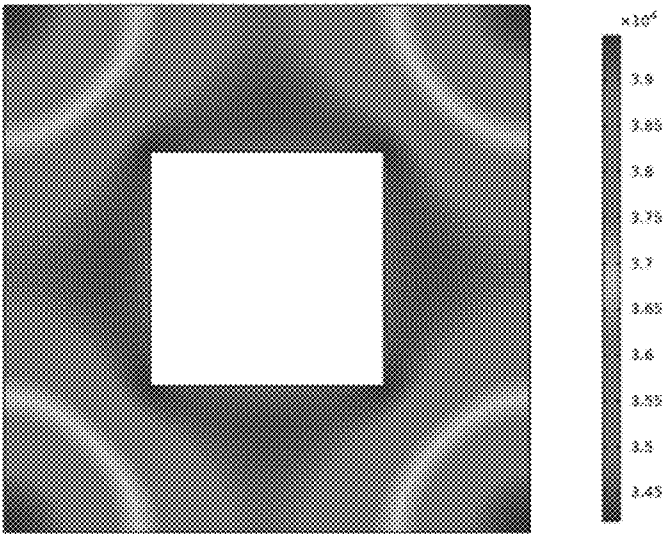
FIG. 10*a* is a schematic diagram of a simulation result of an acoustic pressure field of a culture structure according to an exemplary embodiment of the present disclosure.
Figure 10B:
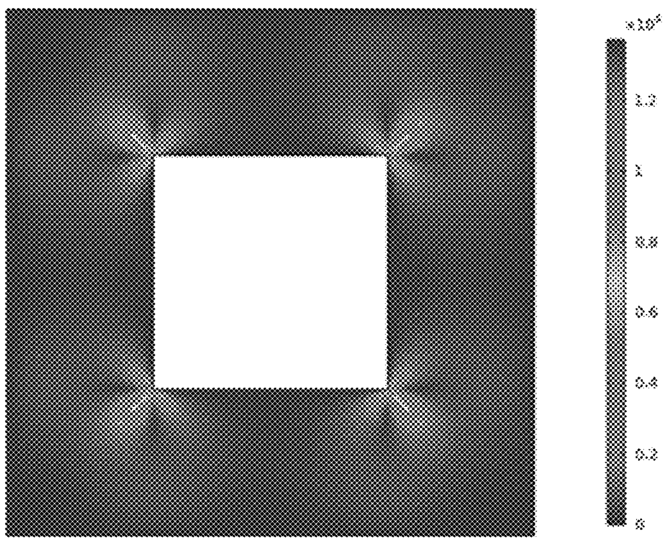
FIG. 10*b* a schematic diagram of a simulation result of an acoustic flow field of a culture structure according to an exemplary embodiment of the present disclosure.
Figure 10C:
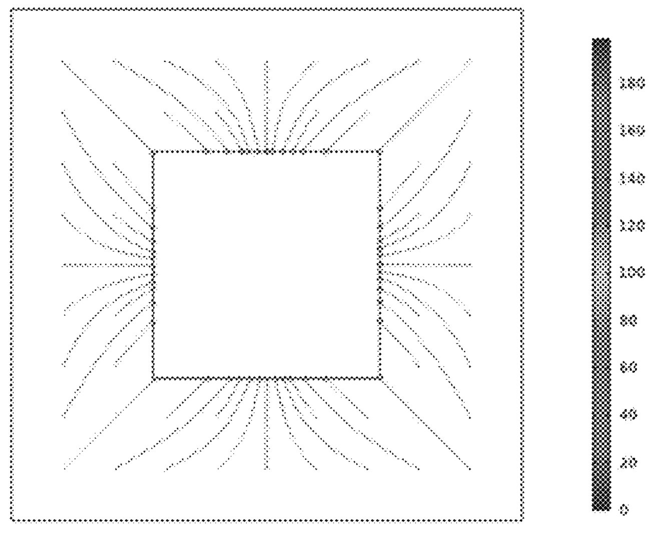
FIG. 10*c* is a schematic diagram of a simulation result of particle tracking trajectories of an acoustic flow field of a culture structure according to an exemplary embodiment of the present disclosure.

The culture structure shown in FIG. 9 is simulated. FIG. 10*a* is a diagram of a simulation effect of an acoustic field of an accommodating structure in the culture structure shown in FIG. 9, where the unit is Mpa. FIG. 10*b* is a diagram of a simulation effect of an acoustic flow field in an accommodating structure in the culture structure shown in FIG. 9, where the unit is mm/S. FIG. 10*c* is a schematic diagram of a simulation result of particle tracking trajectories of particles of 2 mm in an accommodating structures in the culture structure shown in FIG. 9, where the unit is μm/S. According to the simulation results, it can be seen that the culture structure of the embodiment shown in FIGS. 9*a*-9*c* may realize the repeatable sample counting function by dividing the particle samples into four equal parts. For example, the cell counting plate needs to adsorb a fixed volume of liquid to four planes through capillary action. This embodiment may realize fast and effective equal separation and adsorption of larger-sized particles, realize sample counting and particle density measurement, and has a wider application range.

Figure 11A:
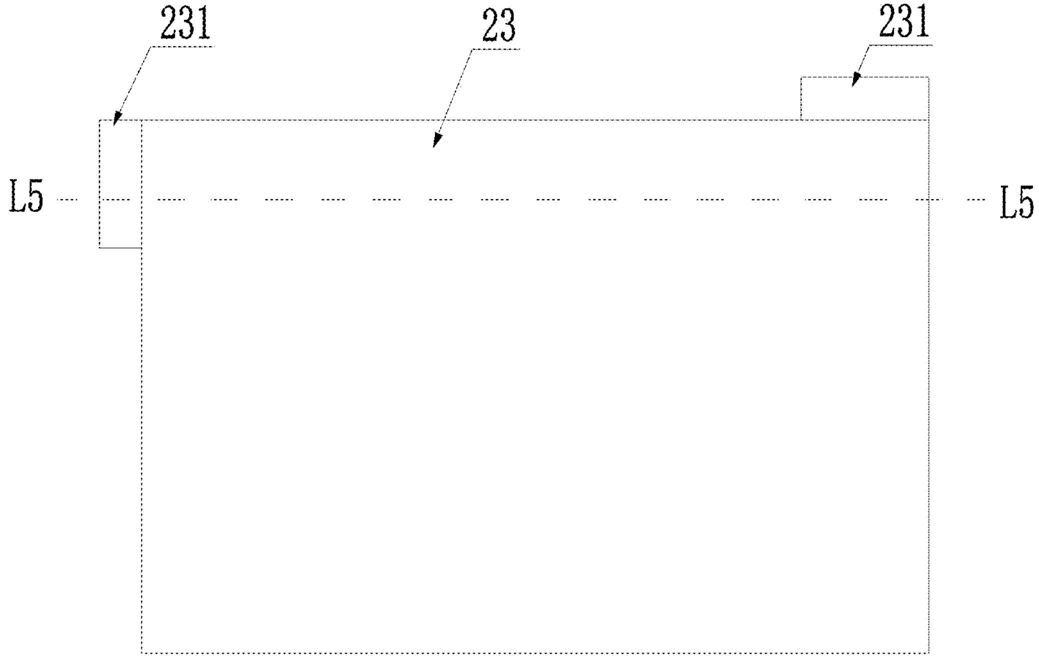
FIG. 11*a* is a schematic diagram of a planar structure of a culture structure according to an exemplary embodiment of the present disclosure.
Figure 11B:
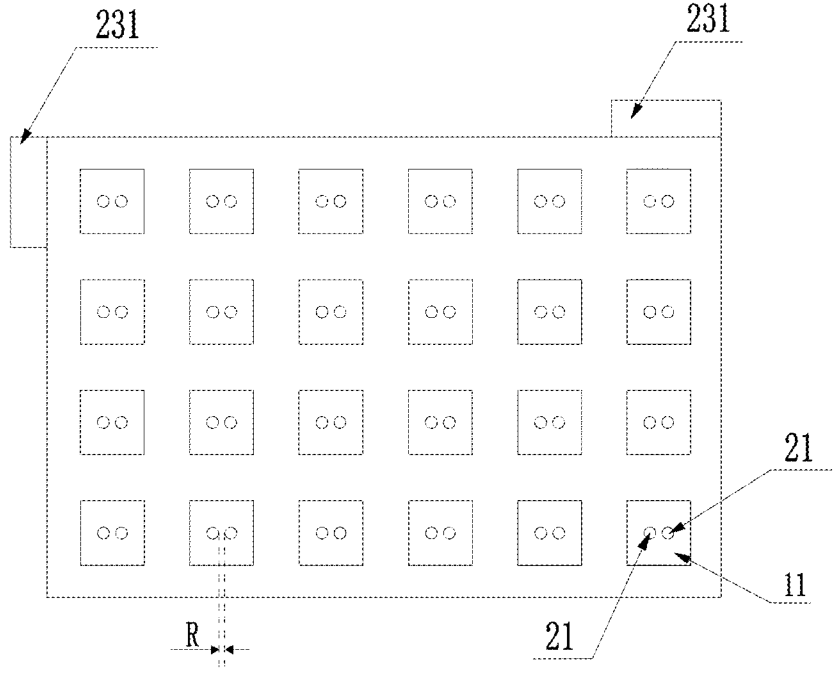
FIG. 11*b* is a schematic diagram of a planar structure of a culture structure shown in FIG. 11*a* with a cover plate removed.
Figure 11C:
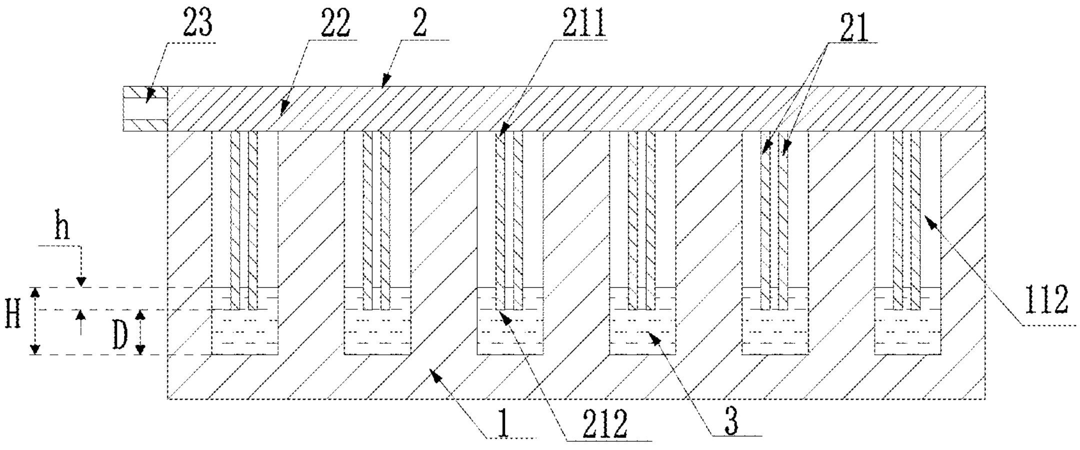
FIG. 11*c* is a schematic diagram of a cross-section structure at a position L5-L5 in FIG. 11*a*.

The culture structure of the embodiment shown in FIGS. 11*a*-11*c* is similar to the culture structure shown in the above embodiments in basic connecting structure and components, but they are different in the structural shape and size. As shown in FIGS. 11*b*-11*c*, the vibration member 21 is a column structure, any one of the accommodating structures 11 is corresponding to two vibration members 21 of column structure, the diameter of the vibration member 21 of column structure is set to 0.2 mm, the spacing R of two vibration members 21 of column structure is 0.2 mm, the accommodating structure 11 is provided as a hollow cuboid structure, the opening of the accommodating structure 11 is square, and the side length of the square opening is 2 mm. A voltage signal of 0.5 V is applied to the two orthogonal piezoelectric transducers 231 of the culture structure of this embodiment, the applied voltage signal intensity (frequency) is 30 kHz, and the phase difference between the two orthogonal piezoelectric transducers 231 is set to 90°. The experiment shows that the particles with a diameter of 1 mm rotate through the whole fluid region within 2000 s and finally concentrate on the two vibration members 21 of column structure. The fluid domain is a liquid coating particles, which, under the action of the vibration member, is removed directly from the vibration member 21 after sufficient movement and stirring in the whole coating liquid.

Figure 12A:
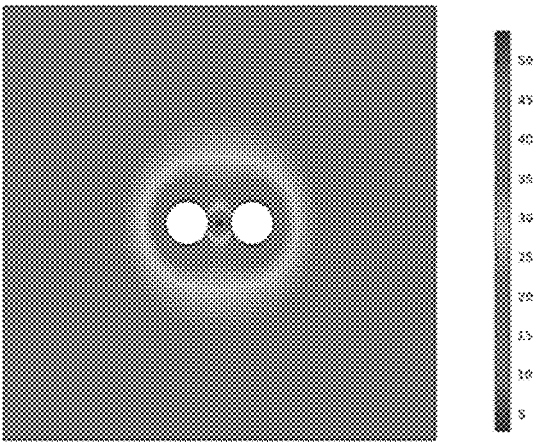
FIG. 12*a* is a schematic diagram of a simulation result of an acoustic pressure field of a culture structure according to an exemplary embodiment of the present disclosure.
Figure 12B:
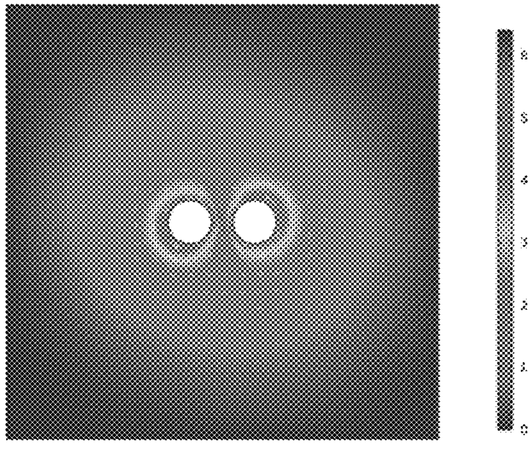
FIG. 12*b* is a schematic diagram of a simulation result of an acoustic flow field of a culture structure according to an exemplary embodiment of the present disclosure.
Figure 12C:
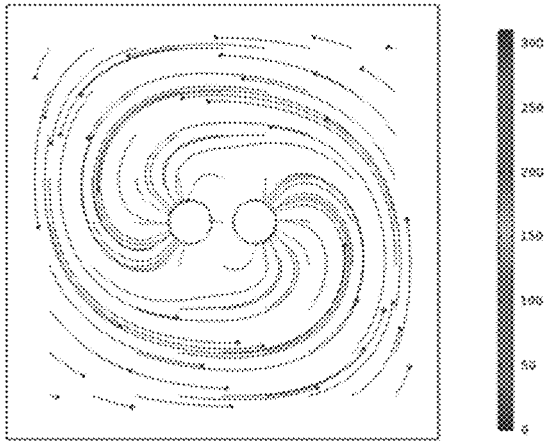
FIG. 12*c* is a schematic diagram of a simulation result of particle tracking trajectories in an acoustic flow field in a culture structure according to an exemplary embodiment of the present disclosure.

The structure shown in FIG. 11 is simulated. FIG. 12*a* is a diagram of a simulation effect of an acoustic field of an accommodating structure in the culture structure shown in FIG. 11, where the unit is Mpa. FIG. 12*b* is a diagram of a simulation effect of an acoustic flow field of an accommodating structure in the culture structure shown in FIG. 11, where the unit is mm/S. FIG. 12*c* is a schematic diagram of a simulation result of particle tracking trajectories of particles with a diameter of 1 mm in an accommodating structures in the culture structure shown in FIG. 11, where the unit is μm/S.

According to the culture structure shown in FIGS. 11*a*-11*c*, two vibration members 21 are provided in a corresponding accommodating structure 11, and a paired column structure is composed of two column structures. The diameter of two end faces of the column structure is selected as 0.2 mm for direct comparison with the embodiment shown in FIGS. 5*a*-5*c*. The selected vibration member of paired column structure has a low pressure region between the paired column structures that the vibration member of a single column structure does not have at all. Combined with the rotating effect of the single column structure in FIGS. 5*a*-5*c*, the acoustic flow field becomes elliptical, the functional effect of the vibration member 21 of the doublecolumn structure in FIGS. 11a-11c may be realizing rapid and uniform stirring in the whole accommodating structure region. For the particles for which surface modification coating needs to be performed, the large-scale elliptical rotation trajectory and the flow stirring may make the surface of the particles fully modified, which has a special technical effect.

In an embodiment of the present disclosure, two fixed orthogonal piezoelectric transducers may be replaced by a plurality of annular piezoelectric transducers fixed at the bottom of the culture plate, the plurality of vibration members 21 may be located at the positions where the bottom of the culture plate 1 is corresponding to the plurality of accommodating structures, and the piezoelectric transducers may be independently controlled by using the TFT, thereby realizing the individual control of each organoid in a single accommodating structure, and achieving a higher modulation depth and regulation accuracy.

An embodiment of the present disclosure further provides a culture method, which adopts the culture structure described in any one of the above embodiments, wherein the culture structure includes a culture plate and a vibration structure, the culture plate includes a plurality of accommodating structures, the accommodating structures are configured to accommodate a culture solution, and the vibration structure includes a vibration signal generating structure and a plurality of vibration members. The method may include following acts: generating a vibration signal; and driving, by the vibration structure, the culture solution in the accommodating structure to move according to the vibration signal.

In an exemplary embodiment, the vibration structure may further include a cover plate, the accommodating structure includes an opening arranged to face a side of the cover plate, the cover plate is provided on a side of the culture plate located at the opening of the accommodating structure, a plurality of vibration members are provided at a side of the cover plate facing the culture plate, any one of the vibration members is arranged corresponding to one of the accommodating structures; the vibration member includes a first end and a second end which are arranged opposite to each other, the first end of the vibration member is connected to the cover plate, the second end of the vibration member extends away from the cover plate into the culture solution of the corresponding accommodating structure; and the vibration signal generating structure is provided on the cover plate.

The act of generating vibration signal includes applying a voltage signal to vibration signal generating structure, generating the vibration signal by the vibration signal generating structure according to the voltage signal.

The act of driving, by the vibration structure, the culture solution in the accommodating structure to move according to the vibration signal, includes: applying the vibration signal to the vibration member through the cover plate, and driving, by the vibration member, the culture solution in the corresponding accommodating structure to move.

An embodiment of the present disclosure further provides a culture chip including the culture structure described in any one of the above embodiments. Therefore, the culture chip has the beneficial effect of the culture structure of any one of the above exemplary embodiments.

Embodiments of the present disclosure provide a culture structure, a culture method, and a culture chip. The culture structure includes a culture plate and a vibration structure, wherein the culture plate includes a plurality of accommodating structures for accommodating culture solution, the vibration structure includes a vibration signal generating structure and a plurality of vibration members, and the plurality of vibration members drive the culture solution in the plurality of accommodating structures to move according to the vibration signal generated by the vibration signal generating structure. According to the culture structure provided by the embodiments of the present disclosure, since the plurality of vibration members drive the culture solution in the plurality of accommodating structures to move according to the vibration signal generated by the vibration signal generating structure, sufficient oxygen may be provided to the organoid in the process of organoid growth, and the oxygen and nutrients in the culture solution are balanced, so that the organoid cultured in the culture solution develop completely, thereby solving the technical problem that the organoid cell dies due to the lack of oxygen or nutrients in the center during the organoid growth.

It should be noted that the structure shape, the size proportion and the like of the culture structure described in the embodiments of the present disclosure are not limited to those described in the above embodiments, and can be adjusted according to actual requirements, and the embodiments of the present disclosure are not limited in this regard. In addition, the drawings of this disclosure are only used to schematically illustrate the structure shape and the approximate proportion, and do not limit the size and the proportion of the microfluidic flow channel structure of this embodiment.

In the description of the embodiments of the present disclosure, it should be understood that an orientation or a position relation indicated by the terms “middle”, “upper”, “lower”, “front”, “rear”, “vertical”, “horizontal”, “top”, “bottom”, “inner”, “outer” and the like is based on the orientation or the position relation shown in the accompanying drawings, which is only for the convenience of describing the present disclosure and simplifying the description, rather than indicating or implying that the device or the element referred to must have the specific orientation, or be constructed and operated in the specific orientation, and thus cannot be interpreted as a limitation on the present disclosure.

In the description of the embodiments of the present disclosure, it should be noted that unless otherwise specified and limited, the terms “mount”, “connected” and “connect” should be understood in a broad sense. For example, a connection may be fixed connection, detachable connection or integrated connection, may be mechanical connection or electrical connection, or may be direct connection, indirect connection through intermediate medium, or communication in two components. Those of ordinary skills in the art may understand meanings of the above-mentioned terms in the present disclosure according to situations.

In the present disclosure, “about” refers to that a boundary is defined not so strictly and numerical values within process and measurement error ranges are allowed.

Although the embodiments disclosed in the present disclosure are as above, the described contents are only embodiments used for convenience of understanding the present disclosure but are not intended to limit the present disclosure. Any person skilled in the art to which the present disclosure pertains may make any modification and variation in forms and details of implementation without departing from the spirit and scope disclosed in the present disclosure. However, the scope of patent protection of the present disclosure is still subject to the scope defined by the appended claims.

The invention claimed is:

1. A culture structure, comprising a culture plate and a vibration structure provided on the culture plate; wherein the culture plate comprises:

a plurality of accommodating structures configured to accommodate a culture solution, wherein each of the plurality of the accommodating structures include an opening;

the vibration structure comprises:

a cover plate comprising a rectangular structure and a lip configured to attach to and surround the culture plate;

a vibration signal generating structure including two piezoelectric transducers, each one of the two piezoelectric transducers is orthogonally disposed along the lip of the cover plate and configured to generate a vibration signal; and a plurality of vibration members have a projecting orthogonal dimension and a length dimension that extends from the surface of the cover plate, and each of the plurality of vibration members comprise a first end and a second end, wherein the first end of each of the plurality of vibration members is connected to the cover plate, and the second end of each of the plurality of the vibration members extend away from the cover plate into one of the plurality of corresponding accommodating structures when the cover plate is attached to the culture plate; and wherein one of the two piezoelectric transducers is each provided along the longer side of the rectangular cover lip and the other one of the two piezoelectric transducers is disposed on the adjacent shorter side of rectangular cover lip, and each of the one of the two piezoelectric transducers applies the vibration signal to propagate through the cover plate and move the plurality of vibration members, wherein the propagation directions of the vibration signals generated by each one of the two piezoelectric transducers intersect with each other along a horizontal plane of the cover plate.

2. The culture structure according to claim 1, and an angle between propagation directions of vibration signals generated by the two piezoelectric transducers is 80° to 100° in the plane where the cover plate is located.

3. The culture structure according to claim 1, wherein each of the two the piezoelectric transducers is an annular piezoelectric transducer; and.

4. The culture structure according to claim 1, wherein a depth of the culture solution is 1 mm to 4 mm, a depth of the each of the plurality of vibration members extend into the culture solution of the corresponding accommodating structure is 0.5 mm to 3 mm, and a distance between each of the plurality of the vibration members and a bottom of the accommodating structure is 0.5 mm to 1.5 mm, when the cover plate is attached.

5. The culture structure according to claim 1, wherein the orthographic dimension of each of the plurality of vibration members on the culture plate are located within a range of orthographic projections of the plurality of accommodating structures on the culture plate, wherein an area of the orthographic projection of the vibration member on the culture plate is 30% to 70% of an area of an orthographic projection of an accommodating structure corresponding to the vibration member on the culture plate.

6. The culture structure according to claim 2, wherein each of the plurality of the vibration members is a vertebral structure, and a cross sectional area of an orthographic projection of a first end of the vibration member on the cover plate is larger than an area of the orthographic projection of a second end of each of the plurality of vibration members on the cover plate, wherein end faces of the first end and the second end of each of the plurality of the vibration members are both circular, a diameter of an end face of the first end of the each of the plurality of vibration members is 0.4 mm to 0.8 mm, a diameter of an end face of the second end of each of the plurality of the vibration members is 0.1 mm to 0.3 mm, and the accommodating structure is a hollow cylindrical structure with an inner diameter between 14 mm to 18 mm.

7. The culture structure according to claim 2, wherein the each of the plurality of vibration members is a column structure, and end faces of a first end and a second end of the column structure are both circular, wherein diameters of the end faces of the first end and the second end of the column structure are 0.1 mm to 6 mm, the accommodating structure is a hollow cylindrical structure or a hollow cuboid structure, an inner diameter of the hollow cylindrical structure is 0.5 mm to 26 mm, an opening position of the accommodating structure of the hollow cuboid structure is square, a side length of the square opening position is 0.5 mm to 26 mm, and a plane where the opening position is located is parallel to a plane where the cover plate is located; and an orthographic projection of the column structure on the cover plate falls within a range of an orthographic projection of the accommodating structure on the cover plate.

8. The culture structure according to claim 7, wherein the diameters of the end faces of the first end and the second end of the column structure are 0.1 mm to 0.4 mm; and the inner diameter of the hollow cylindrical structure is 0.5 mm to 1.5 mm, and the side length of the square opening position is 0.5 mm to 1.5 mm, or, the diameters of the end faces of the first end and the second end of the column structure are 1 mm to 6 mm;

the inner diameter of the hollow cylinder is 10 mm to 26 mm, and the side length of the square opening position is 10 mm to 26 mm, wherein an input voltage signal of a piezoelectric transducer is 0.3 V to 0.8 V, a frequency of the input voltage signal is 25 kHz to 35 kHz, and a phase difference of vibration signals generated by two piezoelectric transducers is −10° to 10° or 80° to 100°.

9. The culture structure according to claim 2, wherein the each of the plurality of vibration members is a cuboid structure, the accommodating structure is a hollow cuboid structure, and an orthographic projection of the accommodating structure on the cover plate covers the orthographic projection of each of the plurality of the vibration members on the cover plate, wherein end faces of a first end and a second end of the cuboid structure are both square, and a side length of the square is 4 mm to 12 mm; and the opening of the each of the plurality of accommodating structures is square, a side length of the square opening position is 14 mm to 22 mm, and a plane where the opening position is located is parallel to a plane where the cover plate is located.

10. The culture structure according to claim 2, wherein each of the plurality of the vibration members is a column structure, end faces of a first end and a second end of the column structure are circular, any one of the accommodating structures is corresponding to two column structures, and orthographic projections of the two column structures on the cover plate are within a range of an orthographic projection of the accommodating structure corresponding to the two column structures on the cover plate, wherein diameters of the end faces of the first end and the second end of the column structure are 0.1 mm to 0.4 mm; and a spacing between two vibration members corresponding to a same accommodating structure is 0.1 mm to 0.3 mm; and each of the plurality of the accommodating structures is a hollow cylindrical structure, and an inner diameter of the hollow cylindrical structure is 1.1 mm to 3.2 mm; or the accommodating structure is a hollow cuboid structure, an opening position of the accommodating structure is a square, a side length of the square opening position is 1.1 mm to 3.2 mm, and a plane where the opening position is located is parallel to a plane where the cover plate is located.

11. The culture structure according to claim 6, wherein diameters of end faces of first ends and second ends of the plurality of vibration members gradually decrease from being close to a piezoelectric transducer to being far away from the piezoelectric transducer.

12. The culture structure according to claim 9, wherein side lengths of end faces of first ends and second ends of the plurality of vibration members gradually decrease from being close to a piezoelectric transducer to being away from the piezoelectric transducer.

13. The culture structure according to claim 1, wherein the vibration signal generating structure comprises a plurality of piezoelectric transducers, the vibration members are located at positions of a bottom of the culture plate corresponding to the plurality of accommodating structures respectively, the plurality of piezoelectric transducers are respectively corresponding to the plurality of vibration members, and the vibration signal generated by each piezoelectric transducer is applied to a corresponding the vibration structure, wherein each of the two piezoelectric transducers is an annular piezoelectric transducer; and an orthographic projection of the each of the piezoelectric transducers on the cover plate is at least partially overlapped with an orthographic projection of the corresponding vibration member on the cover plate.

14. The culture structure according to claim 6, wherein an input voltage signal of a piezoelectric transducer is 0.3 V to 0.8 V, a frequency of the input voltage signal is 20 kHz to 40 KHz, and a phase difference of vibration signals generated by two piezoelectric transducers is 80° to 100°.

15. A culture method, using the culture structure according to claim 1, wherein the method comprises:

generating a vibration signal; and driving, by the vibration structure, the culture solution in each of the plurality of the accommodating structures move according to the vibration signal.

16. The culture method according to claim 15, wherein the generating the vibration signal comprises: applying a voltage signal to the vibration signal generating structure, and generating the vibration signal, by the vibration signal generating structure, according to the voltage signal; and the driving, by the vibration structure, the culture solution in each of the plurality of the accommodating structures to move according to the vibration signal, comprises: applying the vibration signal to the each of the plurality of vibration members through the cover plate, and driving, by the vibration member, the culture solution in the corresponding accommodating structure to move.

* * * * *